United States Patent
Howard

(10) Patent No.: US 11,257,009 B2
(45) Date of Patent: Feb. 22, 2022

(54) SYSTEM AND METHOD FOR AUTOMATED DETECTION OF SITUATIONAL AWARENESS

(71) Applicant: Newton Howard, Providence, RI (US)

(72) Inventor: Newton Howard, Providence, RI (US)

( * ) Notice: Subject to any disclaimer, the term of this patent is extended or adjusted under 35 U.S.C. 154(b) by 0 days.

(21) Appl. No.: 16/557,396

(22) Filed: Aug. 30, 2019

(65) Prior Publication Data

US 2020/0057965 A1 Feb. 20, 2020

Related U.S. Application Data

(63) Continuation of application No. 16/545,205, filed on Aug. 20, 2019.

(60) Provisional application No. 62/783,050, filed on Dec. 20, 2018, provisional application No. 62/726,699, filed on Sep. 4, 2018, provisional application No. 62/719,849, filed on Aug. 20, 2018.

(51) Int. Cl.
*G06N 20/20* (2019.01)
*G06N 5/00* (2006.01)

(52) U.S. Cl.
CPC ............ *G06N 20/20* (2019.01); *G06N 5/003* (2013.01)

(58) Field of Classification Search
CPC .... G06F 3/04842; G06F 9/542; G06F 11/324; G06F 16/287; G06N 20/00; G06N 5/022; G06N 7/005; G06N 3/08; G06N 5/02
See application file for complete search history.

(56) References Cited

U.S. PATENT DOCUMENTS

| | | | |
|---|---|---|---|
| 2009/0006286 A1* | 1/2009 | Angell | G06Q 30/0255 706/12 |
| 2010/0260376 A1* | 10/2010 | Cobb | G06K 9/00771 382/103 |
| 2011/0044533 A1* | 2/2011 | Cobb | G06K 9/00771 382/155 |
| 2013/0111487 A1* | 5/2013 | Cheyer | H04M 1/72563 718/102 |
| 2016/0080419 A1* | 3/2016 | Schiappa | H04L 63/20 726/1 |

OTHER PUBLICATIONS

Hart, P. E.; Nilsson, N. J.; Raphael, 8. (Jul. 1968). "A Formal Basis for the Heuristic Determination of Minimum Cost Paths" IEEE Transactions on Systems Science and Cybernetics SSC4.4 (2): 100-107. doi: 10.1109/TSSC.1 968.300136.

(Continued)

*Primary Examiner* — Yuk Ting Choi
(74) *Attorney, Agent, or Firm* — Michael A. Schwartz

(57) ABSTRACT

Embodiments of the present systems and methods may provide automated techniques that may provide enhanced security and safety and reduced costs. For example, in an embodiment, a method implemented in a computer may comprise receiving, at the computer system, data capturing an event, generating, at the computer system, a narrativization of the data characterizing the event captured in the data, detecting, at the computer system, at least one entity involved in the event captured in the data, obtaining, at the computer system, ontology information based on the generated narrativization and the detected at least one entity, determining, at the computer system, an intent of the at least one detected entity involved in the event captured in the data, and performing, at the computer system, an action responsive to the determined intent.

12 Claims, 25 Drawing Sheets

(56) References Cited

OTHER PUBLICATIONS

Nasser A. EI-Sherbeny, "The Algorithm of the Time-Dependent Shortest Path Problem with Time Windows", Applied Mathematics · Oct. 2014.
S. Kirkpatrick; C. D. Gelati: M. P. Vecchi, "Optimization by Simulated Annealing", Science · Jun. 1983.
Nicholas Metropolis, Arianna W. Rosenbluth, Marshall N. Rosenbluth, Augusta H. Teller, and Edward Teller, "Equation of State Calculations by Fast Computing Machines", J. Chem. Phys. 21, 1087 (Jun. 1953); doi: 10.1063/1.1699114.
Eddy Mayoraz, Ethem Alpaydin, "Support Vector Machines for Multi-Class Classification", IDIAP Research Report 98-06, May 1998.
Iker Yildirim, "Bayesian Inference: Gibbs Sampling", University of Rochester, Aug. 2012.
Marvin Minsky, "The Emotion Machine", Simon & Schuster, New York, 2006.
Stuart Russell and Peter Norvig, "Artificial Intelligence A Modem Approach", Third Edition, Prentice Hall, New Jersey, 2010.
Abraham Silbershatz, Peter B. Galvin, Gerg Gagne, "Operating System Concepts", Ninth Edition, John Wiley & Sons, New Delhi, 2014.

\* cited by examiner

Fig. 2
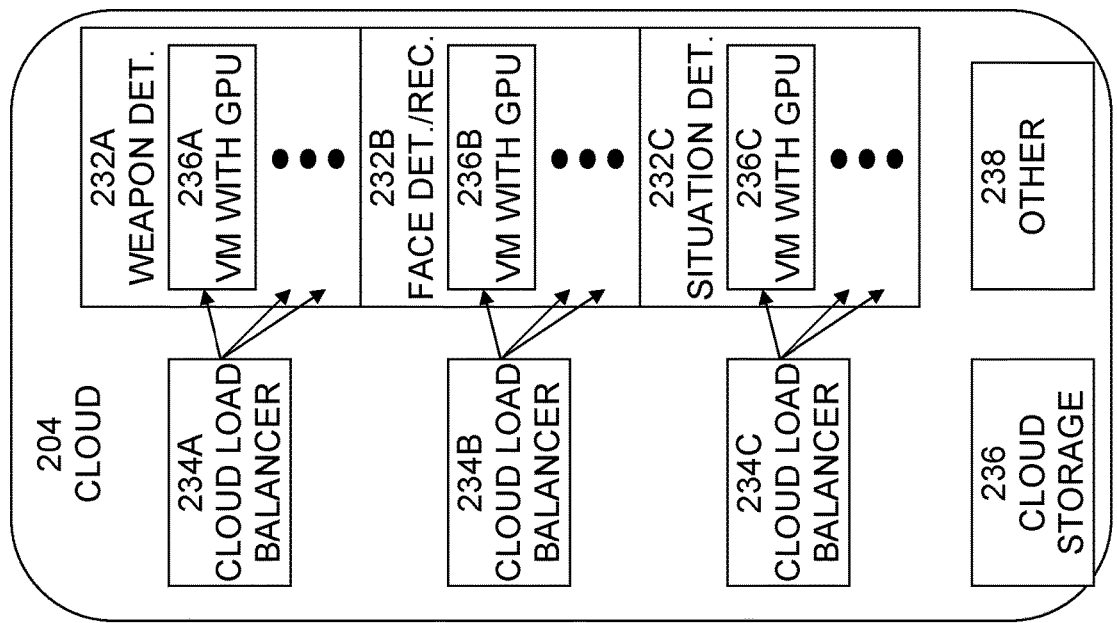
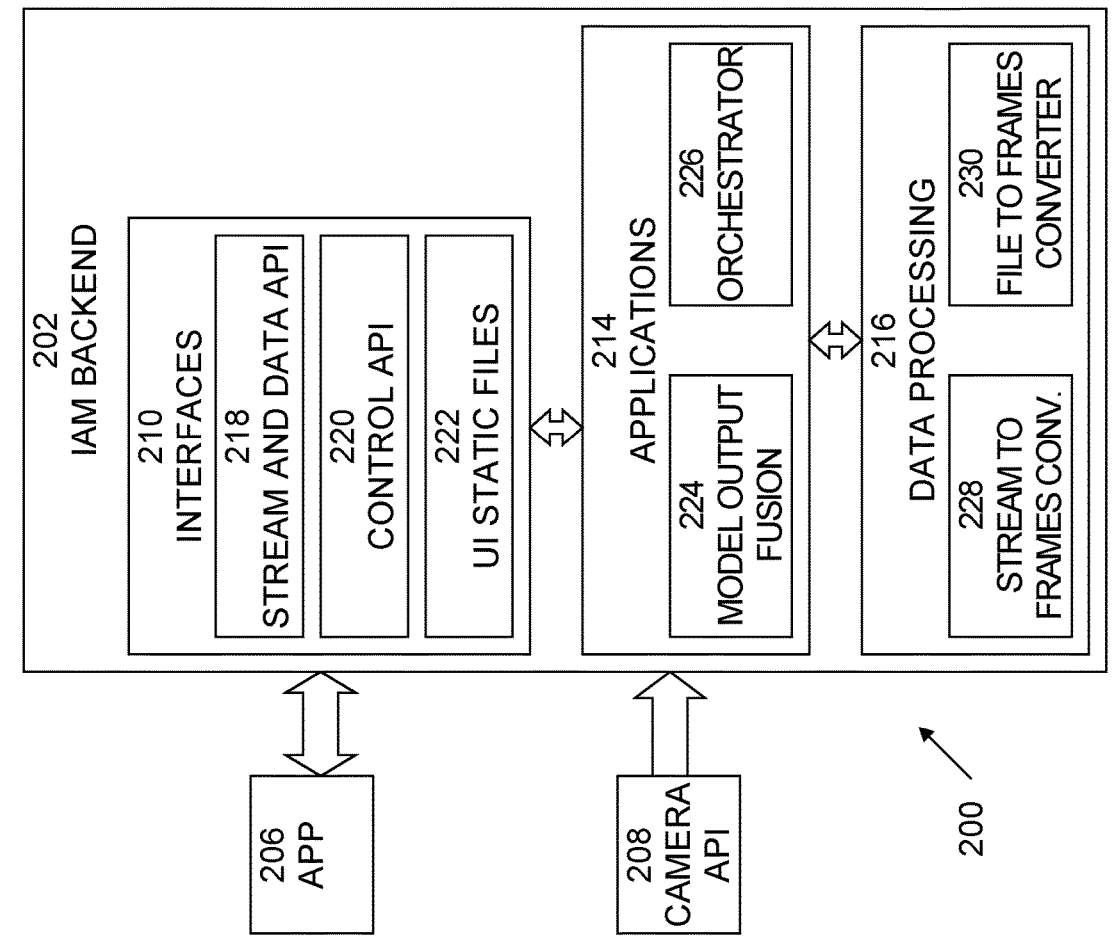

Fig. 10

```
function GENETIC-ALGORITHM(population, FITNESS-FN) returns an individual
  inputs: population, a set of individuals
          FITNESS-FN, a function that measures the fitness of an individual repeat
    new_population ← empty set
    for i = 1 to SIZE(population) do
      x ← RANDOM-SELECTION(population, FITNESS-FN)
      y ← RANDOM-SELECTION(population, FITNESS-FN)
      child ← REPRODUCE(x, y)
      if (small random probability) then child ← MUTATE(child)
      add child to new_population
    population ← new_population
  until some individual is fit enough, or enough time has elapsed
  return the best individual in population, according to FITNESS-FN function REPRODUCE(x, y) returns an individual
  inputs: x, y, parent individuals n ← LENGTH(x); c ← random number from 1 to n
  return APPEND(SUBSTRING(x, 1, c), SUBSTRING(y, c + 1, n))
```

```
function ELIMINATION-ASK(X, e, bn) returns a distribution over X
  inputs: X, the query variable
          e, observed values for variables E
          bn, a Bayesian network specifying joint distribution P(X_1, ..., X_n)

factors ← []
  for each var in ORDER(bn.VARS) do
      factors ← [MAKE-FACTOR(var, e)|factors]
      if var is a hidden variable then factors ← SUM-OUT(var, factors)
  return NORMALIZE(POINTWISE-PRODUCT(factors))
```

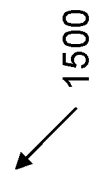
1500

Fig. 16 function LIKELIHOOD-WEIGHTING($X$, e, $bn$, $N$) returns an estimate of $\mathbf{P}(X|\mathbf{e})$
inputs: $X$, the query variable
    e, observed values for variables E
    $bn$, a Bayesian network specifying joint distribution $\mathbf{P}(X_1, \ldots, X_n)$
    $N$, the total number of samples to be generated
local variables: W, a vector of weighted counts for each value of $X$, initially zero for $j = 1$ to $N$ do
    x, $w \leftarrow$ WEIGHTED-SAMPLE($bn$, e)
    W$[x] \leftarrow$ W$[x] + w$ where $x$ is the value of $X$ in x
return NORMALIZE(W)

--- function WEIGHTED-SAMPLE($bn$, e) returns an event and a weight $w \leftarrow 1$; x $\leftarrow$ an event with $n$ elements initialized from e
foreach variable $X_i$ in $X_1, \ldots, X_n$ do
    if $X_i$ is an evidence variable with value $x_i$ in e
        then $w \leftarrow w \times P(X_i = x_i \mid parents(X_i))$
        else x$[i] \leftarrow$ a random sample from $\mathbf{P}(X_i \mid parents(X_i))$
return x, $w$

← 1600

Fig. 17 function GIBBS-ASK(X, e, bn, N) returns an estimate of P(X|e)
local variables: N, a vector of counts for each value of X, initially zero
  Z, the nonevidence variables in bn
  x, the current state of the network, initially copied from e initialize x with random values for the variables in Z
for j = 1 to N do
  for each $Z_i$ in Z do
    set the value of $Z_i$ in x by sampling from $\mathbf{P}(Z_i|mb(Z_i))$
    $N[x] \leftarrow N[x] + 1$ where $x$ is the value of X in x
return NORMALIZE(N)

← 1700

Initialize $x^{(0)} \sim q(x)$
for iteration $i = 1, 2, \ldots$ do
  $x_1^{(i)} \sim p(X_1 = x_1 | X_2 = x_2^{(i-1)}, X_3 = x_3^{(i-1)}, \ldots, X_D = x_D^{(i-1)})$
  $x_2^{(i)} \sim p(X_2 = x_2 | X_1 = x_1^{(i)}, X_3 = x_3^{(i-1)}, \ldots, X_D = x_D^{(i-1)})$
  $\ldots$
  $x_D^{(i)} \sim p(X_D = x_D | X_1 = x_1^{(i)}, X_2 = x_2^{(i)}, \ldots, X_D = x_{D-1}^{(i)})$
end for

← 1702

SYSTEM AND METHOD FOR AUTOMATED DETECTION OF SITUATIONAL AWARENESS

CROSS-REFERENCE TO RELATED APPLICATIONS

This application is a continuation of U.S. patent application Ser. No. 16/545,205, filed Aug. 20, 2019, which claims the benefit of U.S. Provisional Application No. 62/719,849, filed Aug. 8, 2018, U.S. Provisional Application No. 62/783,050, filed Dec. 12, 2018, and U.S. Provisional Application No. 62/726,699, filed Sep. 4, 2018, the contents of all of which are incorporated by reference herein in their entirety.

BACKGROUND

The present invention relates to techniques for providing a Situational Awareness capability through detection of hazardous objects, people, activities, and situations.

Public safety is a top priority for government at all levels—federal, state, and local. In addition, many private companies and organizations prioritize safety of employees, customers, and others.

Typical methods currently employed in monitoring public safety typically do not take full advantage of technological methods, but largely rely on labor intensive techniques, such as security guards, security surveillance cameras, etc. While these techniques may provide some deterrence, they are costly and not entirely effective.

Accordingly, a need arises for automated techniques that may provide enhanced security and safety and reduced costs.

SUMMARY

Embodiments of the present systems and methods may provide automated techniques that may provide enhanced security and safety and reduced costs. For example, embodiments may provide a Situational Awareness capability through detection of hazardous objects, such as a gun, a knife, etc., and through people detection and indication of unknown persons in an area. Embodiments may provide enhanced security and safety in venues such as schools, public events, enterprises, grocery stores, movie theaters, etc.

For example, in an embodiment, a method implemented in a computer comprising a processor, memory accessible by the processor, and computer program instructions stored in the memory and executable by the processor may comprise receiving, at the computer system, data capturing an event, generating, at the computer system, a narrativization of the data characterizing the event captured in the data, detecting, at the computer system, at least one entity involved in the event captured in the data, obtaining, at the computer system, ontology information based on the generated narrativization and the detected at least one entity, determining, at the computer system, an intent of the at least one detected entity involved in the event captured in the data, and performing, at the computer system, an action responsive to the determined intent.

In embodiments, the data capturing an event may comprise at least one of image data, video data, text data, audio data, and sensor data. The data capturing an event may comprise at least one of real-time data relating to events occurring contemporaneously and stored data relating events that occurred in the past. Generating the narrativization may comprise at least one of captioning, at the computer system, image data, captioning, at the computer system, image data video data, recognizing, at the computer system, speech included in audio data, generating summary data, at the computer system, characterizing text data, and generating summary data, at the computer system, characterizing sensor data. Detecting at least one entity may comprise at least one of detecting, at the computer system, the at least one entity comprising at least one of an object, activity, situation, and person from image data using at least one of image object recognition models, image movement recognition models, image facial recognition models, and image situation recognition models, detecting, at the computer system, the at least one entity comprising at least one of an object, activity, situation, and person from video data using at least one of video object recognition models, video movement recognition models, video facial recognition models, and video situation recognition models, detecting, at the computer system, the at least one entity comprising at least one of an object, activity, situation, and person from audio data using at least one of audio object recognition models, audio movement recognition models, audio speaker recognition models, and audio situation recognition models, detecting, at the computer system, the at least one entity comprising at least one of an object, activity, situation, and person from text data using at least one of text object recognition models, text activity recognition models, text situation recognition models, and text person recognition models, and detecting, at the computer system, the at least one entity comprising at least one of an object, activity, situation, and person from text data using at least one of sensor object recognition models, sensor activity recognition models, sensor situation recognition models, and sensor person recognition models.

In an embodiment, a system may comprise a processor, memory accessible by the processor, and computer program instructions stored in the memory and executable by the processor to perform receiving data capturing an event, generating a narrativization of the data characterizing the event captured in the data, detecting at least one entity involved in the event captured in the data, obtaining ontology information based on the generated narrativization and the detected at least one entity, determining an intent of the at least one detected entity involved in the event captured in the data, and performing an action responsive to the determined intent.

In an embodiment, a computer program product may comprise a non-transitory computer readable storage having program instructions embodied therewith, the program instructions executable by a computer, to cause the computer to perform a method comprising receiving, at the computer system, data capturing an event, generating, at the computer system, a narrativization of the data characterizing the event captured in the data, detecting, at the computer system, at least one entity involved in the event captured in the data, obtaining, at the computer system, ontology information based on the generated narrativization and the detected at least one entity, determining, at the computer system, an intent of the at least one detected entity involved in the event captured in the data, and performing, at the computer system, an action responsive to the determined intent.

BRIEF DESCRIPTION OF THE DRAWINGS

The details of the present invention, both as to its structure and operation, can best be understood by referring to the accompanying drawings, in which like reference numbers and designations refer to like elements.

FIG. 2 is an exemplary block diagram of a system, according to embodiments of the present systems and methods.

FIG. 10 is an exemplary illustration of a genetic algorithm, according to embodiments of the present systems and methods.

FIG. 15 is an exemplary pseudocode diagram of an Elimination-Ask process, according to embodiments of the present systems and methods.

FIG. 16 is an exemplary pseudocode diagram of a Likelihood Weighting process, according to embodiments of the present systems and methods.

FIG. 17 is a pseudocode flow diagram of a Gibbs Sampling process, according to embodiments of the present systems and methods.

DETAILED DESCRIPTION

Embodiments of the present systems and methods may provide automated techniques that may provide enhanced security and safety and reduced costs. For example, embodiments may provide a Situational Awareness capability through detection of hazardous objects, such as a gun, a knife, etc., and through people detection and indication of unknown persons in an area. Embodiments may provide enhanced security and safety in venues such as schools, public events, enterprises, grocery stores, movie theaters, etc.

Figure 1:
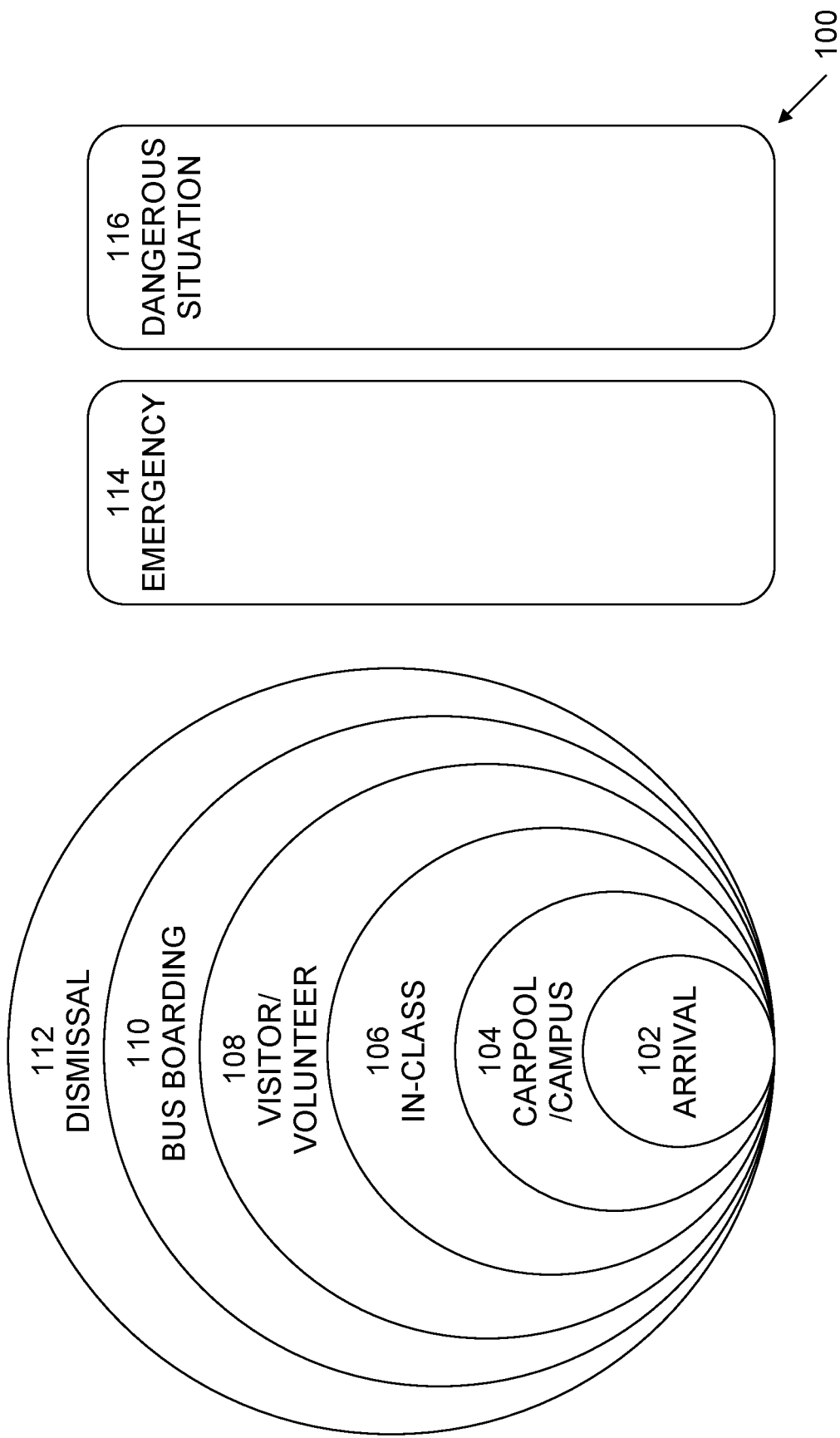
FIG. 1 is an exemplary diagram of venues and situations in which embodiments of the present systems and methods may be utilized.

Examples of venues and situations 100 in which embodiments of the present systems and methods may be utilized are shown in FIG. 1. For example, as shown in FIG. 1, important milestones in a normal school day may include arrival 102 at a venue, such as a school campus, carpool drop-off 104 at the campus, in-class activities 106, visitors and/or volunteer personnel 108, bus boarding 110, dismissal and exit from the campus 112, etc. Further, examples of situations that may be detected by embodiments may include emergency situations 114 and dangerous situations 116. In embodiments, features that may be provided may include a Watch List, Dangerous Object Recognition and Alert, Gun Visual Detection, People recognition, Recorded Video capability, License Plate Detection, Integration with a License Plate Centralized Database, Sex Offender queries, Access System, Record of Visitors/Volunteers, Sentiment Analysis from Facial Recognition, Sentiment Analysis from Voice Recognition, Student Information System (SIS), Safety status and location reporting, Behavior intent recognition, etc.

Described below are a number of embodiments of the present systems and methods. Although embodiments may be described separately, various embodiments may be used in any arrangement—separately, in conjunction with one or more other embodiments, or in combination with one or more other embodiments. In addition, blocks or components of an embodiment may be combined with, or used in conjunction with, other embodiments or blocks or components of one or more other embodiments.

An exemplary block diagram of a system 200, according to embodiments of the present systems and methods, is shown in FIG. 2. System 200 may include an Intention Awareness Manifestation (IAM) backend 202, functionality in cloud 204, one or more user apps 206, and camera application program interface (API) 208. IAM backend 202 may include interfaces 210, applications 214, and data processing 216. Interfaces 210 may include stream and data API 218, control API 220, and user interface (UI) static files 222. Applications 214 may include model output fusion application 224 and orchestrator application 226. Data processing 216 may include stream to frames converter 228 and file to frames converter 230.

Cloud 204 may include a plurality of processing blocks, such as processing blocks 232A-C, a plurality of cloud load balancers 234A-C, cloud storage 236, and other cloud services 238. Each processing block 232A-C may perform one or more type of processing. For example, processing block 232A may perform weapon detection processing, processing block 232B may perform face detection and/or recognition processing, and processing block 232C may perform situation detection processing. Additional processing blocks may perform additional types of processing. Further, each type of processing may be performed by one or more processing blocks. Each processing block may include a plurality of processing resources 236A-C, which may include a plurality of software resources, such as virtual machines (VMs), and a plurality of hardware resources, such as graphics processing units (GPUs). Cloud load balancers 234A-C may distribute processing workload among the plurality of plurality of processing resources 236A-C so as to relatively evenly balance the workload among the plurality of processing resources 236A-C. Such load balancing may provide improved resource use, throughput, response time, reliability, and availability, and may avoid overload of any resources.

Cloud storage 236 may provide computer data storage in which the digital data is stored in logical pools and may spans multiple server that may be in multiple locations. The physical environment is typically owned and managed by a cloud storage providers that is responsible for keeping the data available and accessible, and the physical environment protected and running. Other cloud services 238 may include additional cloud services, such as BigQuery, an interactive dataset analysis service, and Text2World, a cloud text messaging and communication service, etc.

Intention Awareness Manifestation (IAM). Embodiments may provide an intelligent system for the definition, inference and extraction of the persons' intent and aims using a comprehensive reasoning framework for determining intents.

Intent identification becomes significantly important with the increase in technology, the expansion of digital economies and products and diversity in user preferences, which positions a user as a key actor in a system of decisions. Interpretation of such decisions or intent inference may lead to a more open, organized, and optimized society where products and services may be easily adapted and offered based on a forecast of user intent and preferences, such as provided by a recommendation system. Crime and social decay may be prevented using data and intent analysis, such as provided by a prevention system, and the common good may be pursued by optimizing every valuable aspect of user's dynamic lifestyle, such as provided by a lifestyle optimization system. Embodiments may provide these features both at the level of the community and of the individual.

Classification of User Intent. Embodiments may address a number of types of intent, based on duration and form of expression. For example, two classification criteria that may be used include duration and form of expression. For example, duration may include Strategic Intent: that which the user wants to achieve over the long-term in a specific domain (health, social, career, education, etc.) and Tactical Intent: that which the user wants to achieve over the short-term; short term activities. Likewise, form of expression may include Explicit: the intent is explicitly presented to the system and can be directly detected, and Implicit: the intent needs to be derived from one or a combination of data sources that do not express it directly.

The way of detecting and responding to intents may depends on which quadrant they lie in. For example, Explicit Strategic intent may involve a user explicitly expressing a long-term goal, such as "I want to lose weight". In this case, embodiments may confirm and store the strategic intent. Embodiments may give advice on how to achieve the goal, but there are no other immediate steps to take.

Implicit Strategic intent may involve long term goals which embodiments may infer from a user's behavior. For example, if embodiments see that the user steps on a scale daily, a weight related goal may be inferred. Maybe the user wants to lose weight, or wants to bulk up, or just wants to keep a steady weight. Which one of these three scenarios is true must be determined from other signals. Embodiments may not act on these immediately, but may wait for further confirmation from other data channels. When the confidence is high enough, embodiments may prompt the user and ask them about the assumed goal.

Some forms of expression may contain a mix of explicit and implicit structure. For example, the user may say that they would like to get married (the explicit part). The implicit part would come from a dating history which reveals a preference for blondes with blue eyes.

Explicit Tactical intent may usually be immediately answerable by giving recommendations, directions, placing orders and so on. The classic example is "I want to eat", in which case embodiments may suggest nearby restaurants.

It is possible for an intent to be a combination of strategic and tactical. For example, if the user says "I want to go to the gym daily", that is a longer-term intent, not just something they will do now, but at the same time, it is not a goal by itself. Most people don't go to the gym for fun, but because they want to be fit or they want to look different.

Implicit Tactical intent is the case for behaviors where the formulation is not explicit, but embodiments may still give immediate suggestions. If the user says "I'm starving", it means they want to eat. If embodiments notice that the user practices daily on a language flash card app, embodiments may start suggesting related content (this corresponds to tactical, because using the app has a direct influence on learning a language, while stepping on a scale is strategic because it has no direct influence on losing weight).

Embodiments may determine what objects a user interacts with by detecting, for example, common household items from an image. Functionality may include object detection from an image, which may include selecting training data sources (e.g. ImageNet, COCO), selecting image recognition approaches (ex: RCNN, YOLO, SSD), training machine learning (ML) models using ML specific tools, such as transfer learning, hyperparameter search, architecture tuning, etc.

Embodiments may determine what a person does by detecting action from a short image sequence. Functionality may include end to end action detection from video sequences.

Embodiments may determine the persons in a surveyed area and identify each person. Functionality may include object detection and tracking (focus on persons), face recognition, person recognition from video (pose, clothes), person recognition from IoT, security, and other devices, sensor fusion (video, IoT, etc.), etc.

Embodiments may describe the actions in a video sequence to summarize the actions for a time period, such as a day. Functionality may include detecting action from a short image sequence focused only on one actor and to distinguish one action from another. Functionality may include tracking a person through a video sequence, image segmentation, an attention mechanism (in the context of Deep Learning (DL)), application of e2e action detection to parts of an image sequence, etc.

Embodiments may provide alerts when out of the ordinary situations occur. Given a list of daily tasks, can one predict or detect the outliers? Functionality may include automatic altering as manually programming each possible scenario is hard and surely does not cover all the personal preferences. Functionality may include automatically inferring regular patterns of activity and detecting outliers, for example, using process mining, outlier detection from classical machine learning, etc. Based on the model, possible outcomes may be generated.

Embodiments may integrate several data modalities and produce decisions based on them. Ingress may include the output of other data processing subsystems (for example, intent detection, activity detection, geotracking, etc.). Embodiments may provide flexibility and configurability. The actual integration mode of embodiments may vary based on available data and new data streams that are available. Functionality may include expert systems, dense embeddings, Machine Learning algorithms, such as classical and DL based, etc.

Embodiments may provide monitoring of elderly, disabled, and ailing persons in order to detect, for example, a person falling, feeling ill, being in distress, etc. Embodiments may make recommendations to the caregiving personnel regarding a monitored person based on learning the person's routine gestures and objects, so the person's transition from home to care facility is smooth. Functionality may include intent detection, action detection, ML on IoT time series data, including, for example, health monitors, identification of the person, expert systems integrating data from various inputs with health records, detect objects and actions in video feeds, compile a list of most common household objects and habits, answer specific questions about objects/habits, etc. For example, embodiments may distinguish between a grandparent playing hide and seek versus having a stroke.

Embodiments may provide an integrated neighborhood administrator system that may determine what the common habits, behaviors, and activities of the inhabitants are and answer questions about such habits, behaviors, and activities. Embodiments may identify frequent actions and their context. Functionality may include processing multimodal data streams, extracting intent, extracting context (ontologies), extracting actions, extracting objects (video), learning the "culture" of the community by analyzing the processed data, etc. Embodiments may provide answers to questions, such as: Is this administrative policy appropriate for the neighborhood? For example, should an electric car charger be installed in a certain area, when people already park their cars there. For example, providing housing recommendations, "Will my family fit?" or "Where is the best community for me, given my habits?"

Embodiments may provide a security assistant to, for example, identify people wielding hazardous objects and trigger an "alarm". Embodiments may detect certain objects from videos with true positive rate approaching 100%. Objects detected may include, for example, matches, knives, guns, etc.

Embodiments may predict and detect shooting-situations and warn the appropriate responders. Shooting-situation prediction and detection is a very delicate subject: harmful consequences can happen if the detection system is not sensitive and specific enough. Embodiments may provide a multi-component system for shooting situation prediction and detection, making use of the intent detection framework for shooting-intent prediction and using a multi-channel detection system as a fail-safe (shooting-intent-prediction may fail for multiple reasons: gun concealing, missing information, etc.). Shooting-situation detection may use a plurality of data channels (such as audio, video, radio, etc.) for crowd panic detection and shooting-pose recognition.

Embodiments may provide a work-assistant to develop and deploy new apps tailored to the user's needs and objectives. Functionality may include code generation and data processing.

Embodiments may provide health assistant to aid the user by preventing and early-detecting the health issues. Embodiments may utilize health-related data access, genomic data. clinical data, health history data, etc. and may provide health-risk prediction and (early)-diagnosis prediction.

Embodiments may provide a delayed-aging assistant to recommend and facilitate the most up to date practices.

Embodiments may provide a learning assistant to develop user-tailored curricula based on best learning methods and quality, fact-checked content. Functionality may include text comprehension, intent prediction (but we can make it explicit—we don't actually need to predict the learning objective), reviewing learning and research, tracking learning progress, using methods to enhance retention, etc.

Embodiments may provide an automated child supervision system to determine in each moment where the supervised children are and what are their activities. Functionality may include person identification and tracking, action detection, an activity summary for a given period of time with real time push reporting, etc.

Embodiments may provide an Intent extractor and actuator to infer what the appropriate action for a given situation is, given the overall goal of the use case, for example, to keep a particular person safe. Embodiments may use methods that will integrate all the available information and be able to generate an action (even if the action is "do nothing"). Functionality may include expert systems, a policy generators for agents, reinforcement learning, etc. Embodiments may create controlled scenarios with the expected output including "Ideal" scenarios and noisy scenarios and may determine the best channel to express the action, such as text to voice (personal device, automated phone call), IoT device actuators (for example, closing an automated door, ringing an alarm), etc.

Technologies that may be used to implement components of embodiments of the present systems and methods may include Semantic Networks/Knowledge Graphs such as BabelNet, ConceptNet, Google Knowledge Graph, WordNet, etc., which may be used for hierarchical intent dataset creation (standalone and combined with other sources). A subset of this database may represent a portion of a hierarchical intent database.

Embodiments of the present systems and methods may be well suited to providing IAM functionality due to the large diversity of data channels and types together with the high complexity and interrelatedness of different ontologies that are involved.

Figure 3A:
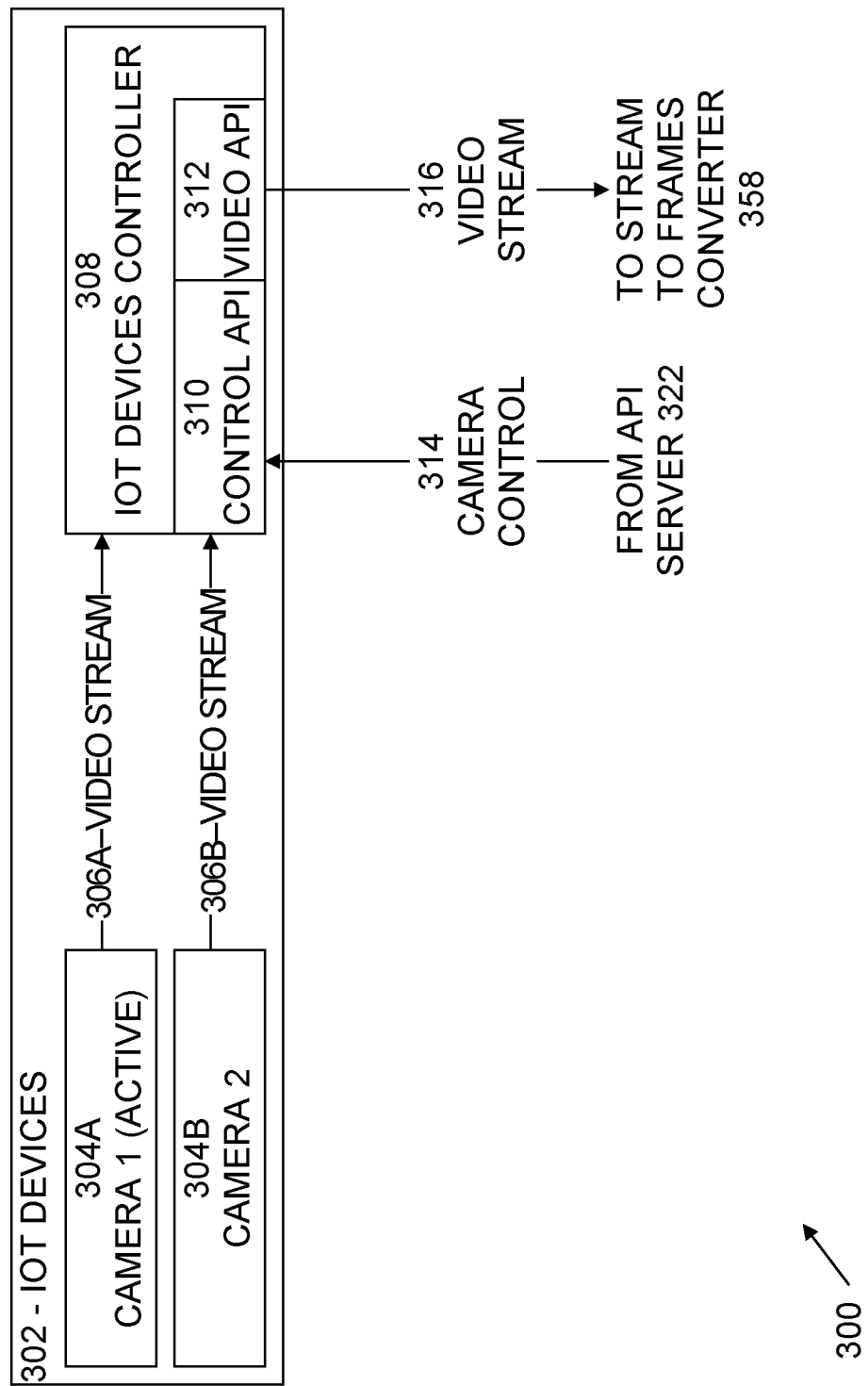
FIGS. 3a-b are an exemplary block diagram of a system, according to embodiments of the present systems and methods.
Figure 3B:
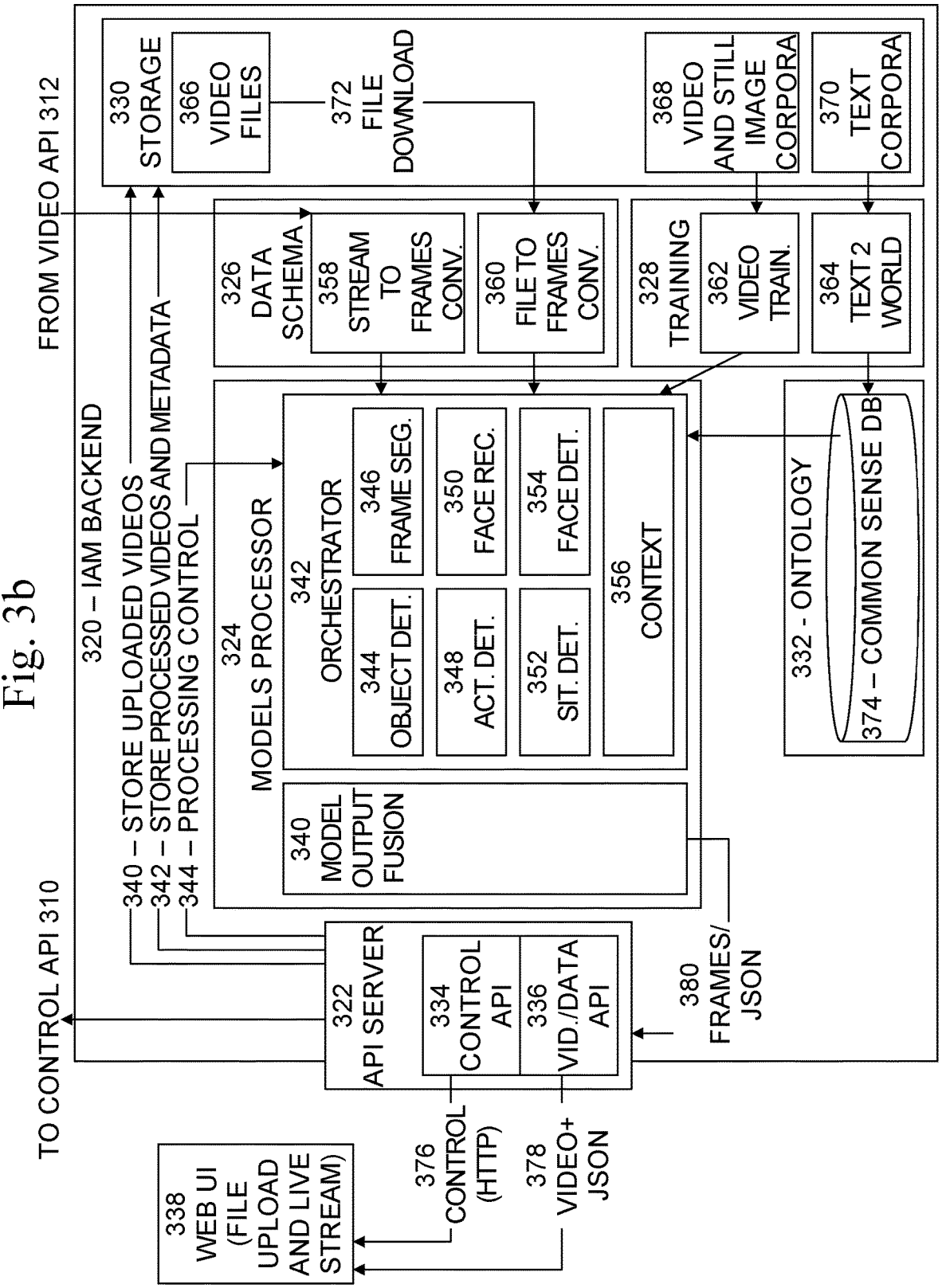

An exemplary block diagram of a system 300, according to embodiments of the present systems and methods, is shown in FIGS. 3a-b. In the example shown in FIG. 3a, system 300 may include a plurality of Internet of Things (IoT) devices 302, such as cameras 304A-B, and one or more IoT devices controller 308. Each camera may transmit a video stream to IoT devices controller 308. For example, camera 1 304A may transmit video stream 306A to IoT devices controller 308 and camera 2 304B may transmit video stream 306B to IoT devices controller 308. IoT devices controller 308 may include control API 310 and video API 312. Control API 310 may communicate camera control data with API server 322, shown in FIG. 3b. Video API 312 may transmit video streams 316 from one or more of cameras 304A-B to stream to frames converter 358, shown in FIG. 3b.

Turning now to FIG. 3b, IAM backend 320 is shown. IAM backend 320 may include API server 322, models processor 324, data schema 326, training block 328, storage block 332, and ontology block 332. API server 322 may include control API 334 and video/data API 336. API server 322 may communicate with a user interface (UI), such as Web UI 338, which may provide the capability for a user to, for example, upload files and live stream video. Control API 334 may communicate control data 376 with Web UI 338, while video/data API 336 may communicate video streams 378, using, for example, JavaScript Object Notation (JSON). As noted above, API server 322 may communicate camera control data with control API 310, shown in FIG. 3a. API server 322 may store and retrieve uploaded videos 340 with storage 330, store and retrieve processed videos and metadata 342 with storage 330, and communicate processing control data with models processor 324. Likewise, API server 322 may communicate frames 380, using, for example, JavaScript Object Notation (JSON).

Model processor 324 may include model output fusion block 340 and orchestrator 342. Model output fusion block 340 may obtain or receive output from a plurality of models and may generate a combination, ensemble, or fusion of the output that may provide better accuracy, reliability, confidence, etc. over the output from individual models. Orchestrator 342 may include object detection block 344, frame segmentation block 346, activity detection block 348, face recognition block 350, situation detection block 352, face detection block 354, and context block 356. Object detection block 344 may perform detection of specified objects in images or video streams. Such specified objects may include, for example, weapons, such as guns, knives, etc., objects that may hold weapons or contraband, such as backpacks, cases, etc., people, animals, vehicles or any other object or type of object that may be specified. For example, such object detection processing may be performed using artificial intelligence or machine learning models that may be included in or used by object detection block 344. Frame segmentation block 346 may perform segmentation of images or frames of video streams, so as to divide the images or frames into segments including different objects or types of objects and/or for separate processing. For example, such object detection processing may be performed using artificial intelligence or machine learning models that may be included in or used by frame segmentation block 346.

Activity detection block 348 may perform detection of different types of activities based on the positions, arrangements, and movement of people and objects in the images or video stream. For example, such object detection processing may be performed using artificial intelligence or machine learning models that may be included in or used by activity detection block 348. Face recognition block 350 may perform recognition of faces detected by face detection block 354. Face detection block 354 may detect faces using artificial intelligence or machine learning models that may be included in or used by face detection block 354. Face recognition block 350 may recognize faces using artificial intelligence or machine learning models that may be included in or used by face recognition block 350, and may additionally use facial data identifying or associated with faces of large numbers of persons.

Situation detection block 352 may perform detection of different types of situations based on the positions, arrangements, and movement of people and objects in the images or video stream. For example, such situation detection processing may be performed using artificial intelligence or machine learning models that may be included in or used by situation detection block 352. Context block 356 may augment or supplement detection performed by blocks 344-354 using contextual information relating to the people, objects, activities, and/or situations detected by blocks 344-354. For example, such contextual information may include text message to, from, or relating to the people, objects, activities, and/or situations obtained for example, from Text2World, a cloud text messaging and communication service, social media, email, etc.

Storage 330 may include video files 366, video and still image corpora 368, and text corpora 370. Video files 366 may include video streams that have been stored for later reference and analysis. Video and still image corpora 368 may include stored video streams and images that may be used to train models included in the blocks of models processor 324. Likewise, text corpora 370 may include stored text that may be used to train models included in the blocks of models processor 324. Video and still image corpora 368 and text corpora 370 may be obtained from a number of sources, such as public and proprietary image, video, and text repositories, Internet crawling, special purpose data generation, etc.

Data schema block 326 may include stream to frames converter 358 and file to frames converter 360. File to frames converter 360 may receive file downloads 372 from video files 366 stored in storage 330 and may convert file downloads 372 to frames for processing by models processor 324. Likewise, stream to frames converter 358 may receive video streams 316 from video API 312 and may convert video streams 316 to frames for processing by models processor 324.

Ontology block 332 may include common sense database 374.

Figure 4A:
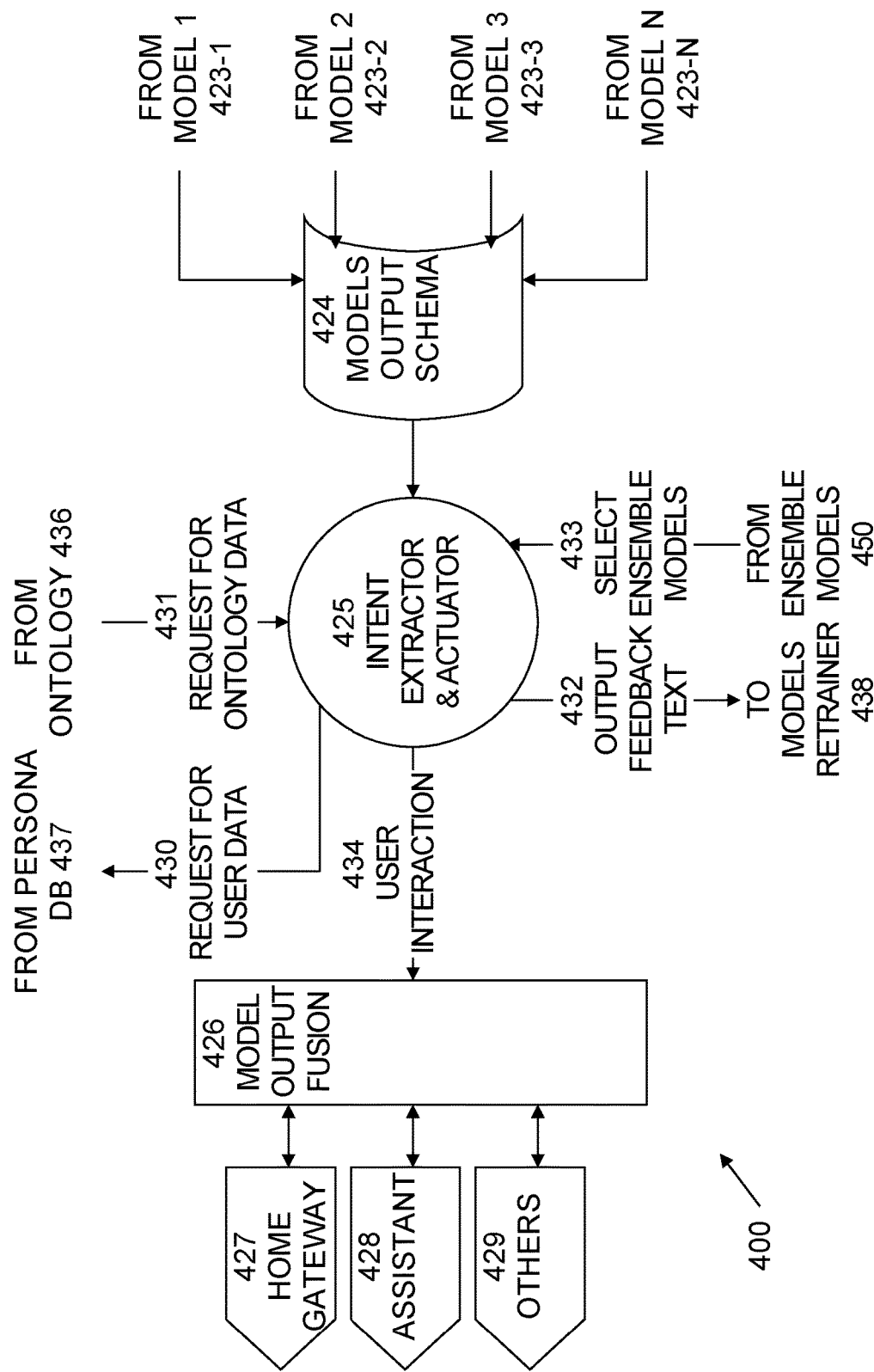
FIGS. 4a-d are a block and data flow diagram of a system, according to embodiments of the present systems and methods.
Figure 4B:
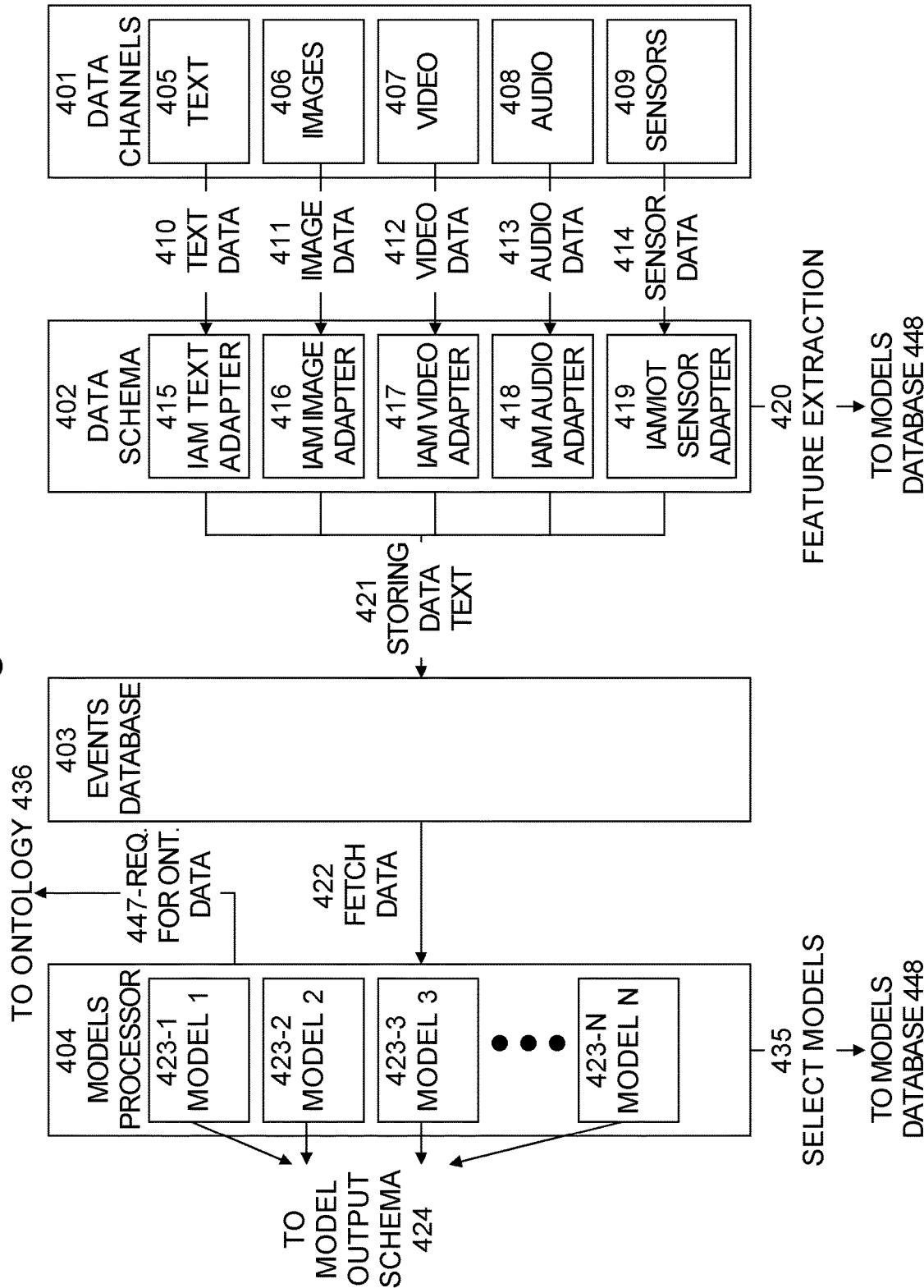

An exemplary block and data flow diagram of a system 400, according to embodiments of the present systems and methods is shown in FIGS. 4a-d. Referring first to FIG. 4b, system 400 may include data channels 401, data schema 402, events database 403, and models processor 404. Data channels 401 may include data-capturing points associated with types of data: video 407, image 406, text 405, audio 408, sensors 409, etc. The data channels layer may include several stages of data retrieval and manipulation, such as: identification of input points and types for each data channel, retrieval of data and data preprocessing, and data sampling techniques and storage. Further, data channels 401 may determine for each context what data channels 405-409 are available. Data from data channels 401, such as text data 410, image data 411, video data 412, audio data 413 and sensor data 414 may be input to data schema 402.

Data schema 402 may include IAM text adapter 415, IAM image adapter 416, IAM video adapter 417, IAM audio adapter 418, and IAM/IoT sensor adapter 419. Adapters 415-419 may receive their respective data 410-414 and may convert the received data to one or more common formats and may perform feature extraction on the converted data. The results 420 of the feature extraction may be communicated with models database 448. The converted data from adapters 415-419 may be sent for storage in events database 403, which may store the converted, but otherwise raw data 410-414.

Data may be fetched 422 for processing from events database 403 and sent to models processor 404. Models processor 404 may include a plurality of models such as models 423-1, 423-2, 423-3 through 423-N. For example, each model 423-1-423-N may be a particular type of model, such as is described below, and may handle a particular type of data. However, all models 423-1-423-N may include any type of model and may handle any type of data. Models processor 404 may select models 424 from model database 448 for advanced feature extraction and processing depending on the available events that may be stored in events database 403. Further, models processor 403 may use sequences of models. The models selected and processed 435 by models processor 404 may be sent to models output schema 424.

Turning now to FIG. 4a, shown are models output schema 424, intent extractor and actuator 425, model output fusion 426, home gateway 427, assistant 428, and others 429. Models output schema 424 may receive, for example, selected models 423-1-423-N from models processor 424 and may arrange the features of the selected models according to a common format for further processing. The models in the common format may be sent to intent extractor and actuator 425. Intent extractor and actuator 425 may select and use ensemble models 433 to process user data 430 requested from persona database 437, ontology data requested from ontology block 436 and extracted features for intent prediction. Intent extractor and actuator 425 Intent extractor and actuator 425 may output feedback text 432 to be sent to models retrainer 438. Intent extractor and actuator 425 may output the extracted intent, as specified or modified by user interaction 434, to model output fusion block 426. Model output fusion block 426 may obtain or receive features extracted from a plurality of models and may generate a combination, ensemble, or fusion of the features that may provide better accuracy, reliability, confidence, etc. over the features extracted from individual models. The output extracted intent may be sent to consumers of such information, such as home gateways 427, personal assistants 428 or other devices or apps, and other consumers, such as security systems, administrator systems, etc.

Figure 4C:
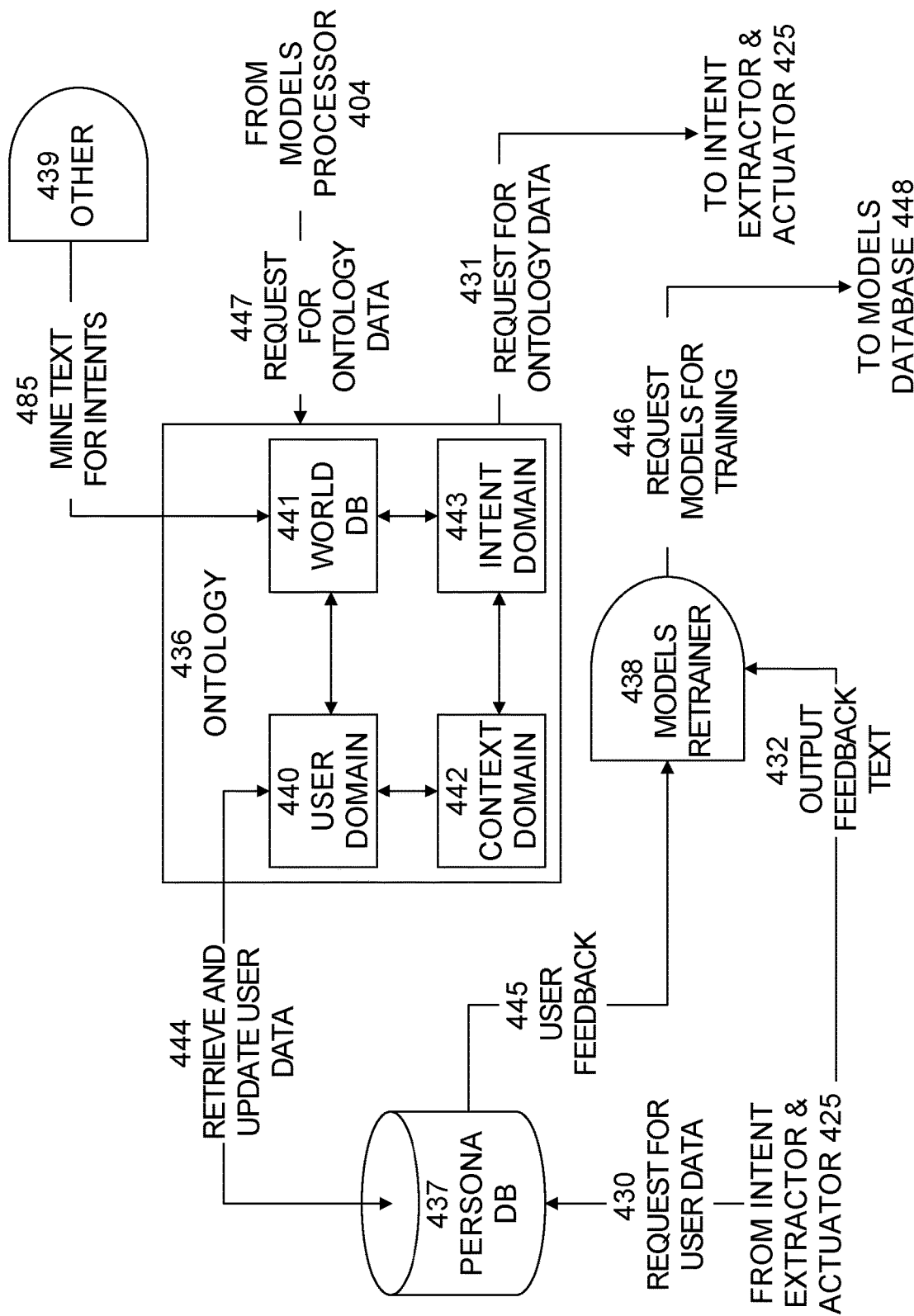

Turning now to FIG. 4c, shown are ontology block 436, persona database 437, models retrainer 438, and other services 439. Ontology block 436 may include user domain 440, world database 441, context domain 442, and intent domain 443. User domain 440 may include ontology data including concepts and categories relating to users of the system and may include data showing the properties and the relations between the users and their data. World database 441 may include data about the real world obtained from any private or publicly available source, such as the Internet. Context domain 442 may include ontology data including concepts and categories relating to the context of data in the system and may include data showing the properties and the relations between the contexts and the other data. Intent domain 443 may include ontology data including concepts and categories relating to intents of people who may be monitored by the system and may include data showing the properties and the relations between the those people, their actions, their characteristics, etc. Ontology block 436 may provide requested ontology data 431 to intent extractor and actuator 425 and may provide requested ontology data 447 to models processor 404. Persona database 437 may include data relating to users of the system, including their identities, characteristics, online or offline behavior, etc. User domain 440 of ontology block 436 may retrieve and update user data 444 stored in persona database 437. Intent extractor and actuator 425 may request user data 430 from persona database 437. Models retrainer may receive user feedback 445 from persona database 437 and feedback text 432 from intent extractor and actuator 425 to initiate and control retraining of models stored in model database 448. Such retraining may be initiated and controlled, for example, by requesting models for training 446 from model database 448. Other services 439 may include services such text processing functions that may mine text for intents 485.

Figure 4D:
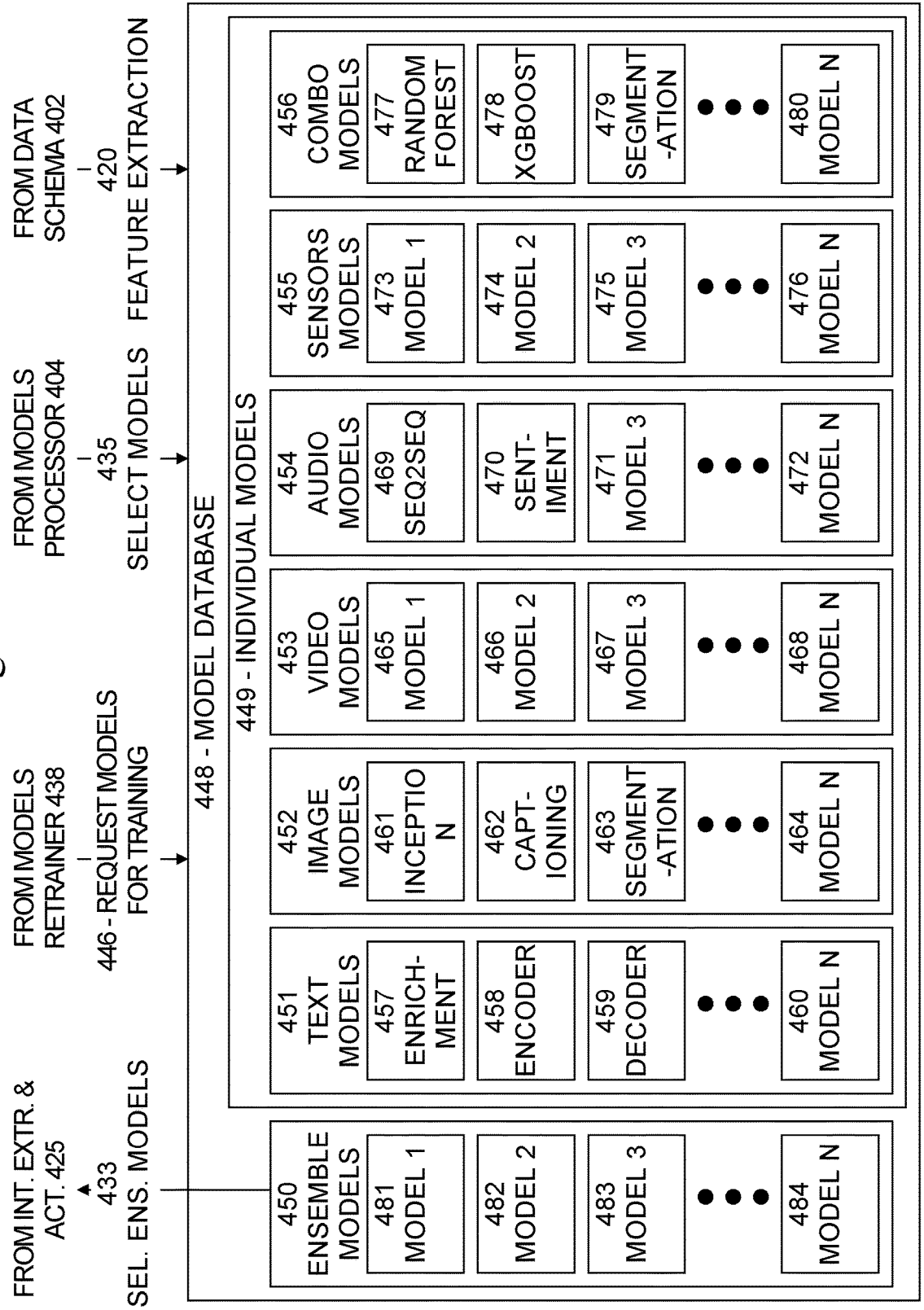

Turning now to FIG. 4d, shown is model database 448. Model database may include individual models 449 and ensemble models 450. Individual models 449 may include various models for handling different types of data. For example, individual models 449 may include text models 451, for processing text data, image models 452, for processing image data, video models 453, for processing video data, audio models 454, for processing audio data, sensors models, for processing data from sensors, and combo models 456, for processing data of combinations of types or sources. Text models 451 may include, for example, enrichment models, which may improve or refine the text data, encoder models, which may reduce the input dimensions and compress the input data into an encoded representation, decoder models, which may decompress encoded data into an plaintext representation, and additional models 460, which may perform additional processing of text data. Image models 452 may include inception models 461, which may have filters with multiple sizes operating on the same level, captioning models 462, which may automatically caption images, segmentation models 463, which may divide images into different portions for processing or based on objects in each segment, and additional models 464, which may perform additional processing of image data. Video models 453 may include a plurality of models 465, 466, 467, 468, which may be used to process video streams. Audio models may include seq2seq 469, which may provide encoding and decoding and functions such as Machine Translation, Text Summarization, Conversational Modeling, Image Captioning, etc., sentiment models 470, which may perform sentiment analysis, opinion mining, or emotion detection using natural language processing, text analysis, computational linguistics, and biometrics to identify, extract, quantify, and study affective states and subjective information, and additional models 471, 472, to process audio data. Sensors models 455 may include a plurality of models 473, 474, 475, 476, which may be used to process data streams from a variety of sensors. Combination models 456 may use multiple learning algorithms to obtain better predictive performance than could be obtained from any of the constituent learning algorithms alone and may include random forest models 477, which may perform classification, regression, and other analysis using a plurality of decision trees, XGBoost models 478, which may provide gradient boosting models, segmentation models 479, and other combination models 480. Ensemble models 450 may include a plurality of models 481, 482, 483, 484, which may provide combinations of models that may outperform individual models.

Figure 5:
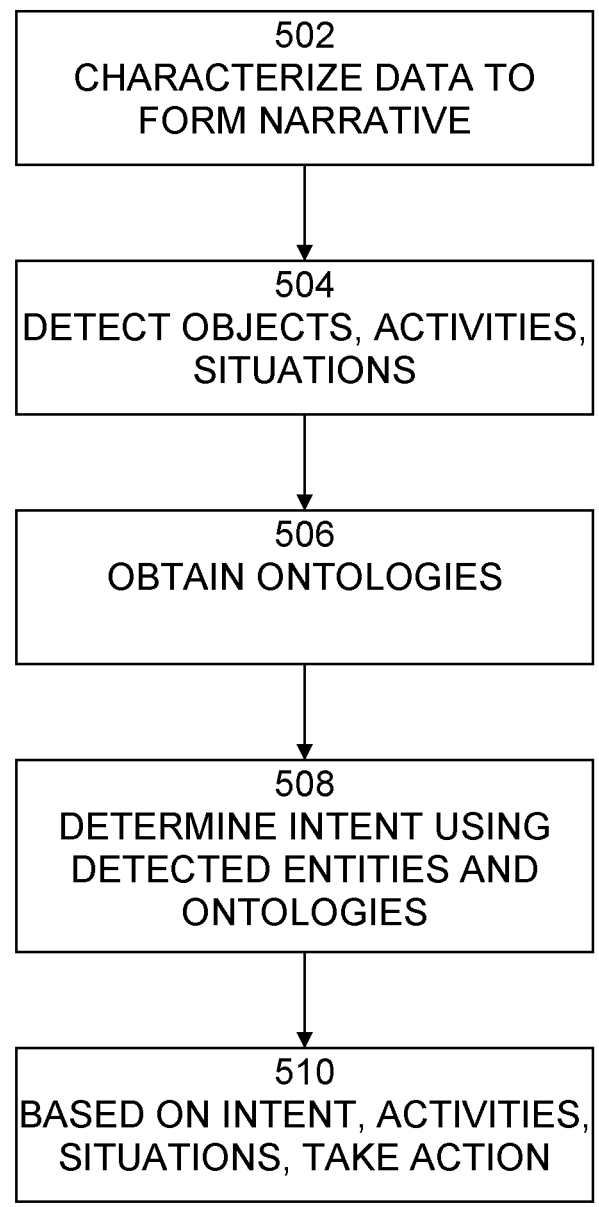
FIG. 5 is an exemplary process of intent extraction from incoming data, such as images, video, text, audio, sensor data, according to embodiments of the present systems and methods.

An exemplary process 500 of intent extraction from incoming data, such as images, video, text, audio, sensor data, etc., is shown in FIG. 5. Process 500 may begin with 502, in which the incoming data relating to events including persons, objects, activities, and/or situations, such as images, video, text, audio, sensor data, etc., may be characterized to form a narrative or metadata describing the events occurring in the data. The incoming data may be live, streaming, real-time data relating to events occurring contemporaneously, the incoming data may be stored data relating events that occurred in the past, or the data may include both live and stored data. For example, for image or video data, captioning algorithms, such as captioning models 462, shown in FIG. 4d, may be run on the images or frames of the video to obtain a narrativization of the images or video. For audio data, speech recognition algorithms, such as seq2seq models 469, may be run to obtain a narrativization of the audio. Likewise, text models 451 or sensors models 455 may be run on text data or sensor data, respectively, to generate summaries characterizing the incoming data.

Action recognition from an image or sequence of images to recognize the action performed in an image or a sequence of images. The recognized action may be a tactical intent to which embodiments may respond, or may be an action that can be used in conjunction with the ontology ensemble to infer strategic intent.

For example, Tran et al. 2015 have used 3-dimensional convolutional networks for action recognition on Sport1M (Joe Yue-Hei Ng et al. 2015) and UCF101 (Wang and Gupta 2015) datasets with accuracies of 90.8% and 85.2%, respectively. Wang and Gupta 2015; Wang et al. 2016 have introduced a framework for video-based action recognition employing temporal segment networks. They have obtained good accuracies for action recognition on the HMDB51 (Kuehne et al. 2011) (69.4%) and UCF101 (94.2%) datasets.

Action prediction in a sequence of images may be performed to predict what are the most probable actions performed by an actor in a sequence of images. The predicted action may be a tactical intent to which embodiments may respond, or may be an action that can be used in conjunction with the ontology ensemble to infer strategic intent. Koppula and Saxena 2013 have obtained an activity prediction accuracy of 75.4%, 69.2% and 58.1% for an anticipation time of 1, 3 and 10 seconds respectively.

Narrativization may be performed to extract a phrasal or an intermediate numerical representation (embeddings, feature vectors) from an image of an ordered sequence of images. To be able to obtain a collection of words describing the objects/activities in an image, embodiments may pass through an intermediate numerical representation in a dense vector space (so called "image features" in the context of deep learning). This intermediate numerical representation may be processed into a more domain specific pipeline that can determine the relations between agents, activities, and objects. Embodiments may use an implementation similar to the work of Fast et al. 2016.

At 504, entities, such as objects, activities, situations, persons, etc. may be detected and recognized from the data. For example, for image or video data, image object recognition models, image movement recognition models, image facial recognition models, and image situation recognition models, or using video object recognition models, video movement recognition models, video facial recognition models, and video situation recognition models, etc., which may be included in image models 452 and/or video models 453 may be run to detect and recognize objects, activities, situations, persons, etc. from the images or video. For audio data, audio object recognition models, audio movement recognition models, audio speaker recognition models, and audio situation recognition models, which may be included in audio models 454 may be run to detect and recognize objects, activities, situations, persons, etc. from the audio using audio object recognition models and audio speaker recognition models. Likewise, text models 451 or sensors models 455 may be run on text data or sensor data, respectively, to identify and recognize objects, activities, situations, persons, etc. from the data, using text object recognition models, text activity recognition models, text situation recognition models, and text person recognition models, etc., or using sensor object recognition models, sensor activity recognition models, sensor situation recognition models, and sensor person recognition models, etc., respectively.

At 506, ontology information may be obtained, for example, from ontology block 436. The characterizations from 502 and the identifications from 504 may be used to obtained relevant and related ontology information.

At 508, intent may be determined using the previously obtained characterizations from 502, the identifications from 504, and ontology information from 506. At 510, based on the determined intent, activities, situations, etc., appropriate action may be taken. For example, dangerous or threatening intent, activities, situations, etc. may cause embodiments to alert police, security, the fire department, etc.

Figure 6A:
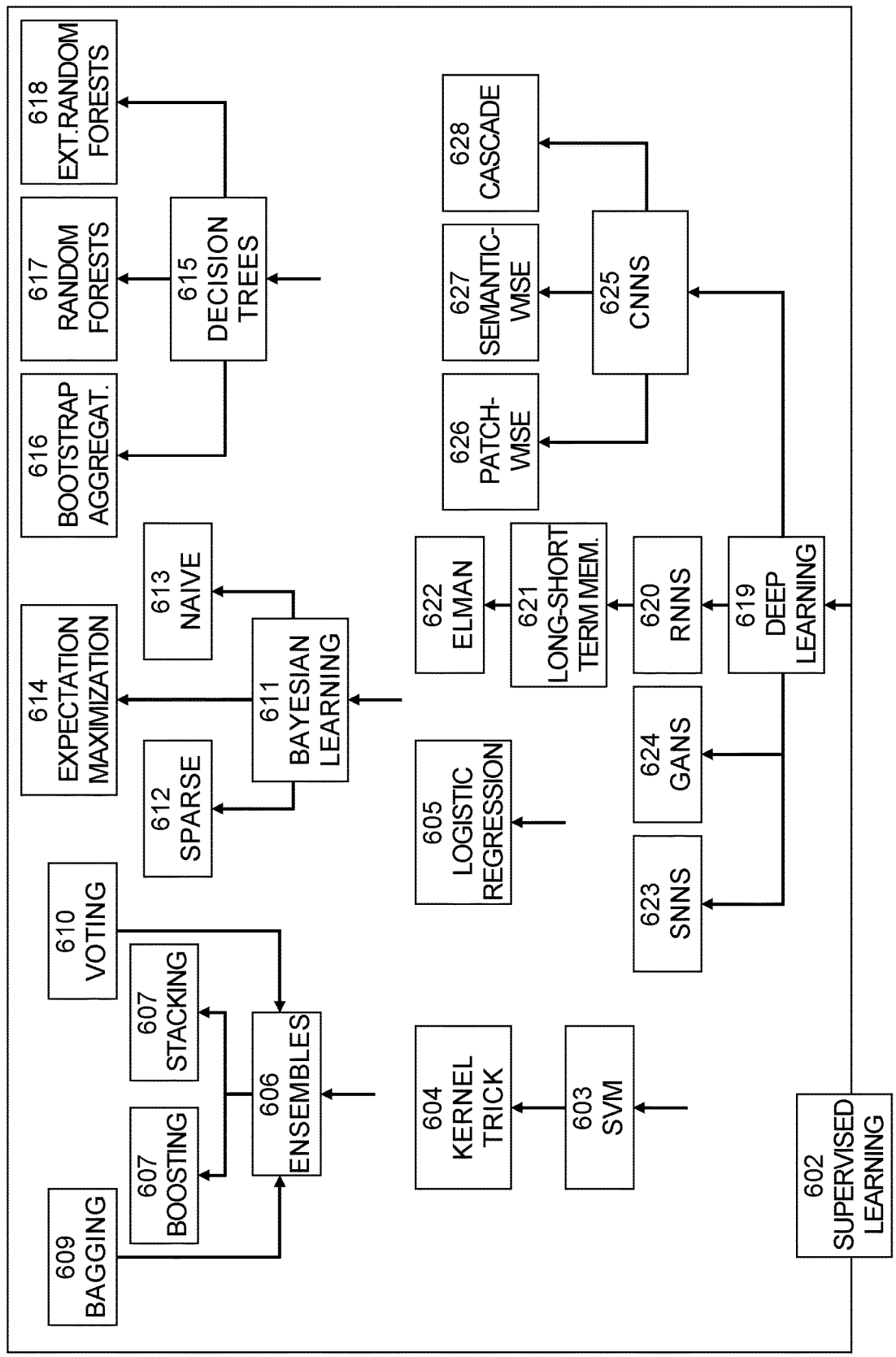
FIGS. 6a-c are an exemplary block diagram of an Orchestrator architecture, according to embodiments of the present systems and methods.
Figure 6B:
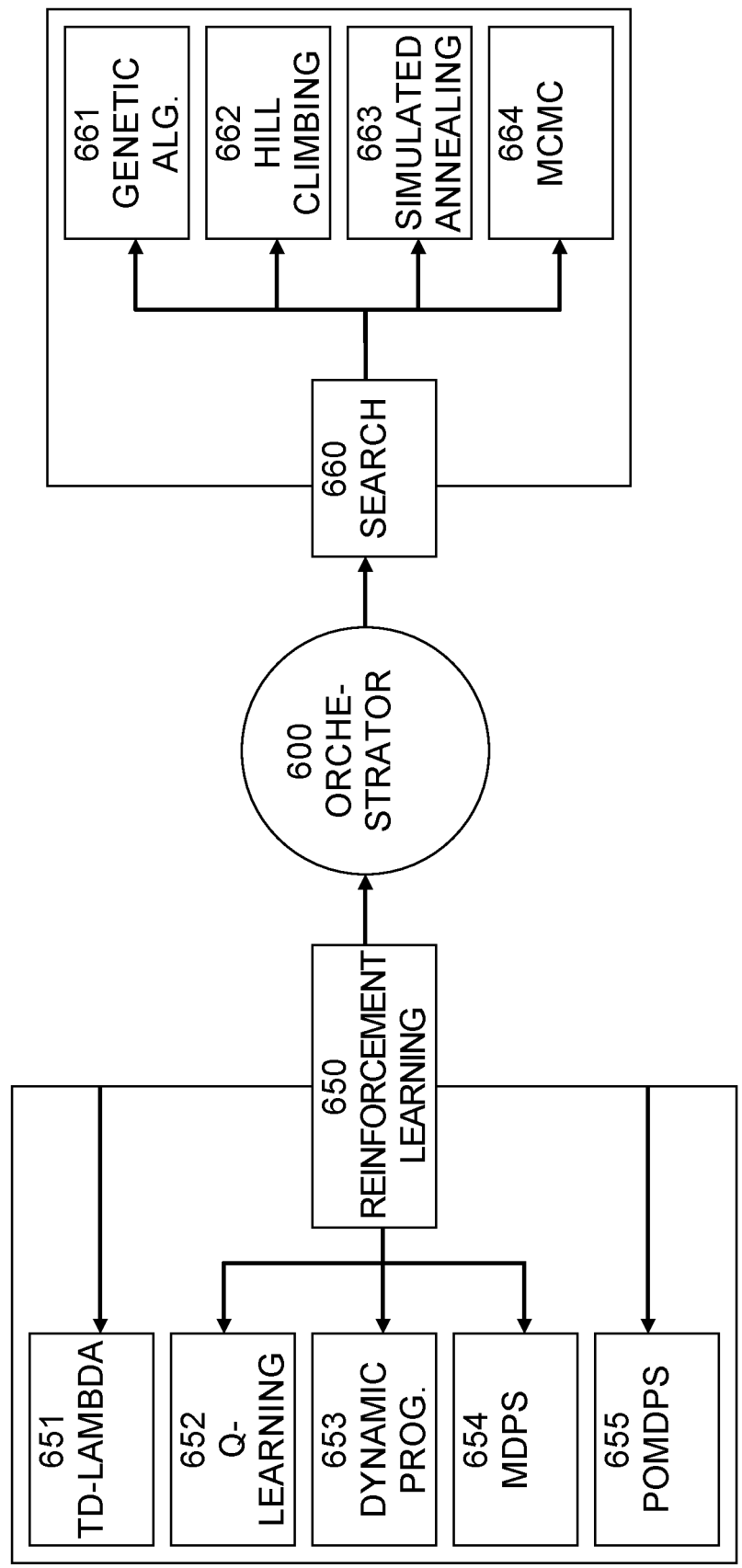
Figure 6C:
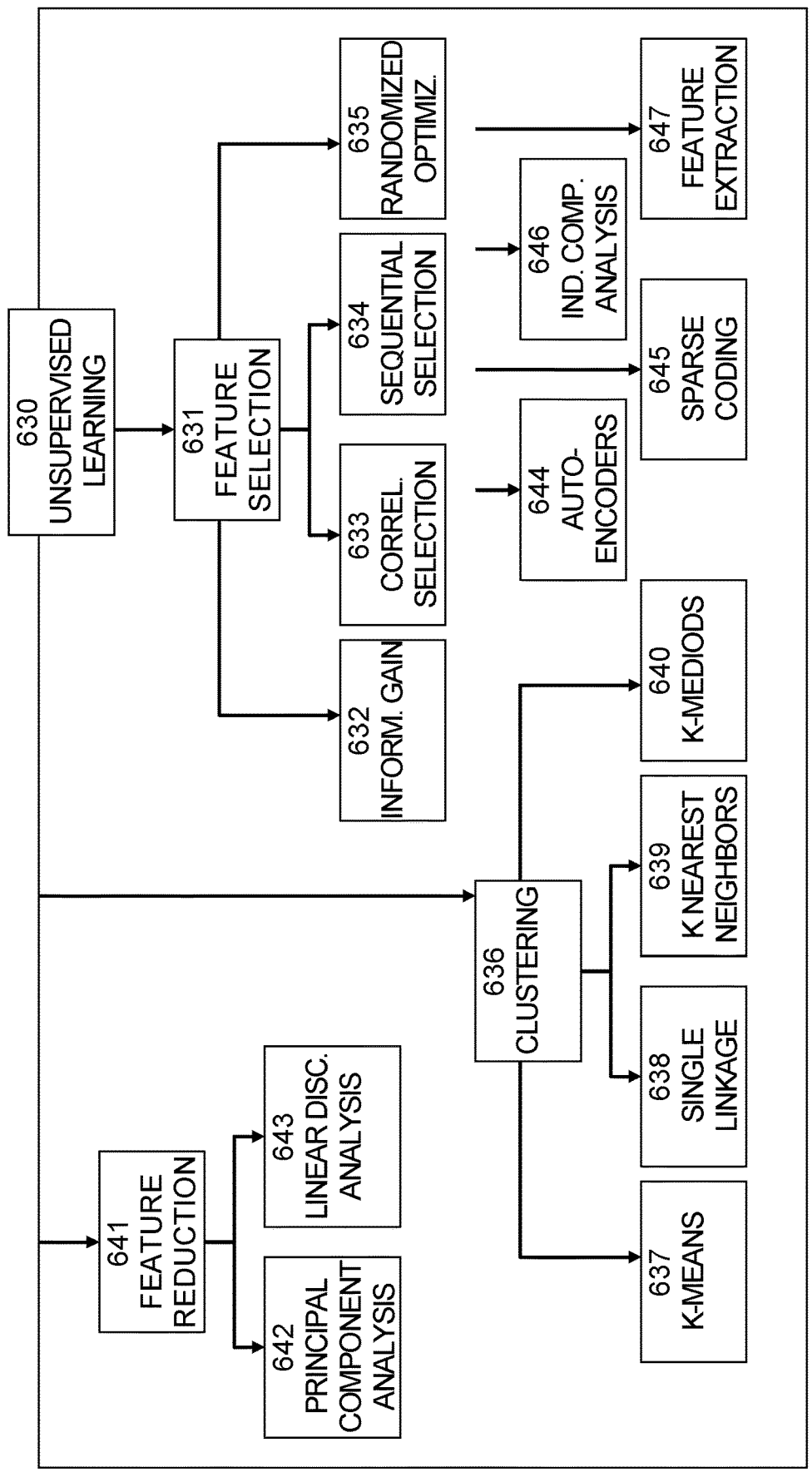

FIGS. 6a-c are an exemplary block diagram of an orchestrator architecture, such as that shown at 324 of FIG. 3b, or that may be used in conjunction with, or as part of system 200, shown in FIG. 2, or may be used in conjunction with, or as part of system 400, shown in FIG. 4. For example, as shown in FIG. 6a, embodiments may utilize Supervised learning models 602, such as Support Vector Machines models (SVMs) 603, kernel trick models 604, linear regression models (not shown), logistic regression models 605, Bayesian learning models 611, such as sparse Bayes models 612, naive Bayes models 613, and expectation maximization models 614, linear discriminant analysis models (not shown), decision tree models 615, such as bootstrap aggregation models 616, random forest models 617, and extreme random forest models 618, deep learning models 619, such as random, recurrent, and recursive neural network models (RNNs) 620, long-short term memory models 621, Elman models 622, generative adversarial network models (GANs) 624, and simulated, static, and spiking neural network models (SNNs) 623, and convolutional neural network models (CNNs), such as patch-wise models 626, semantic-wise models 627, and cascade models 628.

For example, as shown in FIG. 6c, embodiments may utilize Unsupervised learning models 630, such as Clustering models 636, such as hierarchical clustering models (not shown), k-means models 637, single linkage models 638, k nearest neighbor models 639, k-medioid models 640 mixture models (not shown), DBSCAN models (not shown), OPTICS algorithm models (not shown), etc., feature selection models 631, such as information gain models 632, correlation selection models 633, sequential selection models 634, and randomized optimization models 635, feature reduction models, such as principal component analysis models 642 and linear discriminative analysis models 643, autoencoder models 644, sparse coding models 645, independent component analysis models 646, feature extraction models 647, Anomaly detection models (not shown), such as Local Outlier Factor models (not shown), etc., Deep Belief Nets models (not shown), Hebbian Learning models (not shown), Self-organizing map models (not shown), etc., Method of moments models (not shown), Blind signal separation techniques models (not shown), Non-negative matrix factorization models (not shown), etc., For example, as shown in FIG. 6b, embodiments may utilize Reinforcement learning models 650, such as TD-lambda models 651, Q-learning models 652, dynamic programming models 653, Markov decision process (MDP) models 654, partially observable Markov decision process (POMDP) models 655, etc. Embodiments may utilize search models 660, such as genetic algorithm models 661, hill climbing models 662, simulated annealing models 663, Markov chain Monte Carlo (MCMC) models 664, etc. Likewise, Model Ensembler component 470 may determine whether there is a combination of models that can outperform the selected model using any type of machine learning model.

Figure 7:
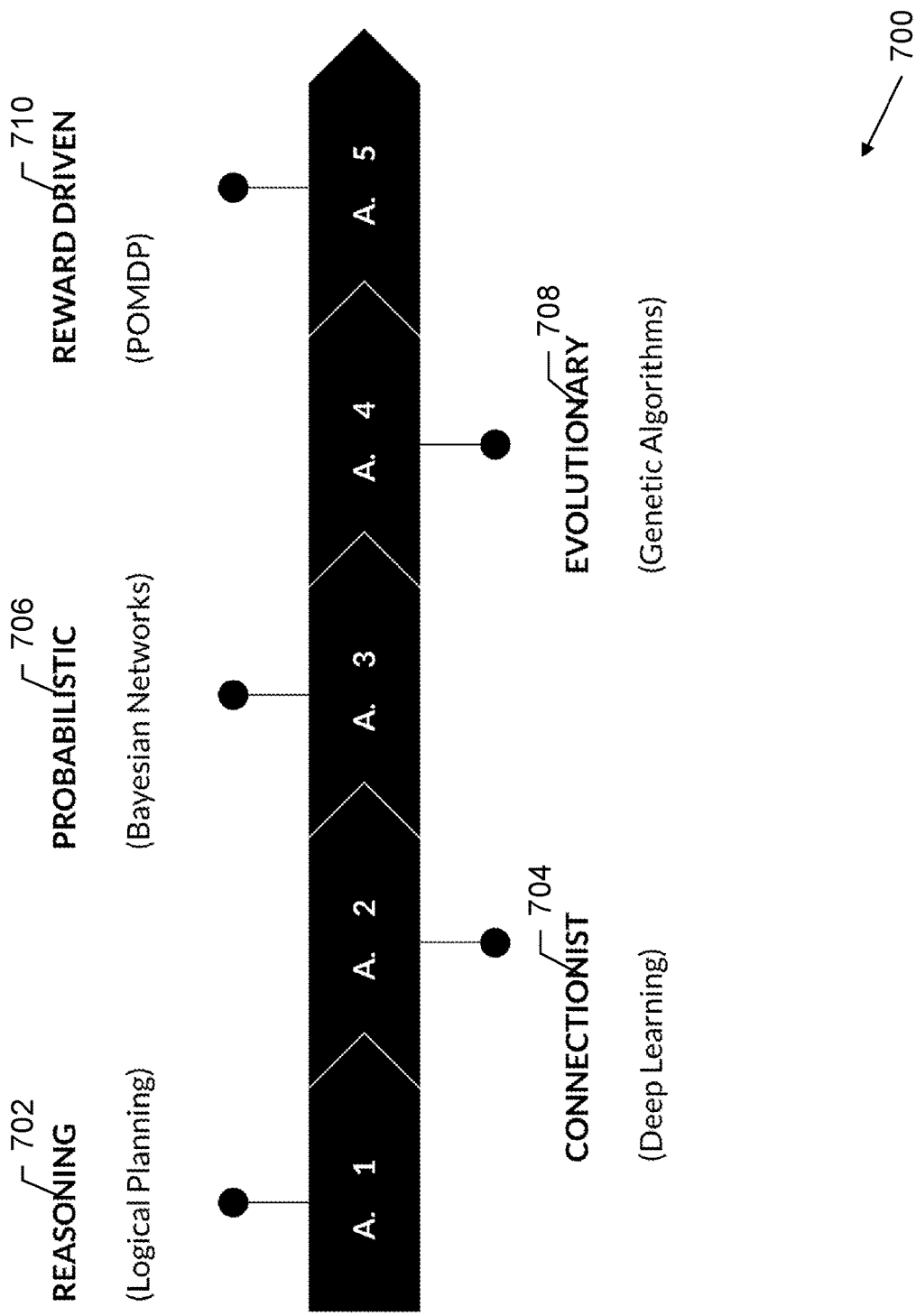
FIG. 7 is an exemplary illustration of processing workflow, according to embodiments of the present systems and methods.

An example of general approaches 700 (and a specific example from each one of them) that can be combined in the processing workflow of embodiments of the present system and methods is shown in FIG. 7. Approaches 700 may include reasoning/logical planning 702, connectionist/deep learning 704, probabilistic/Bayesian networks 706, evolutionary/genetic algorithms 708, and reward driven/partially observable Markov decision process (POMDP) 710.

Genetic Algorithms 708 have been applied recently to the field of architecture search, mainly in the case of deep learning models. Due to improvements in hardware and tweaks in the algorithm implementation, these methods may show good results.

Figure 8:
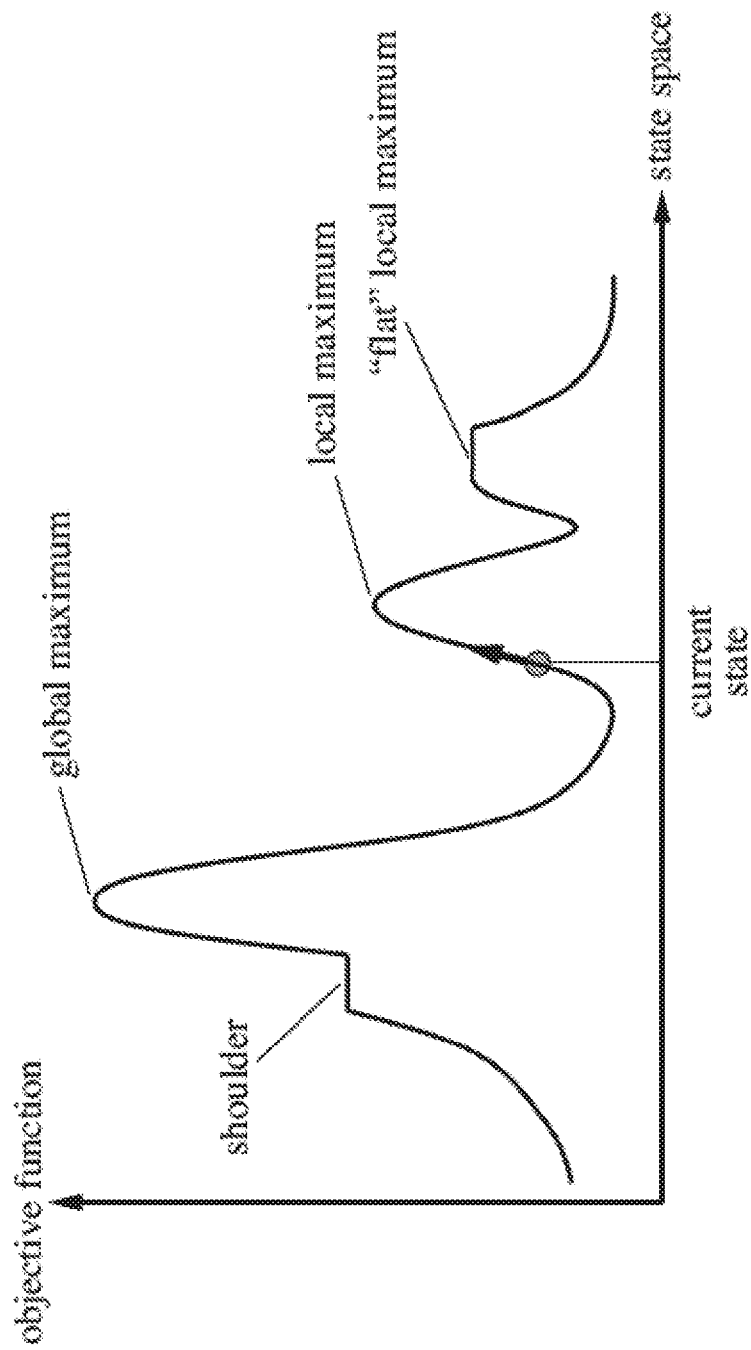
FIG. 8 is an exemplary representation of a family of genetic algorithms, according to embodiments of the present systems and methods.
Figure 9:
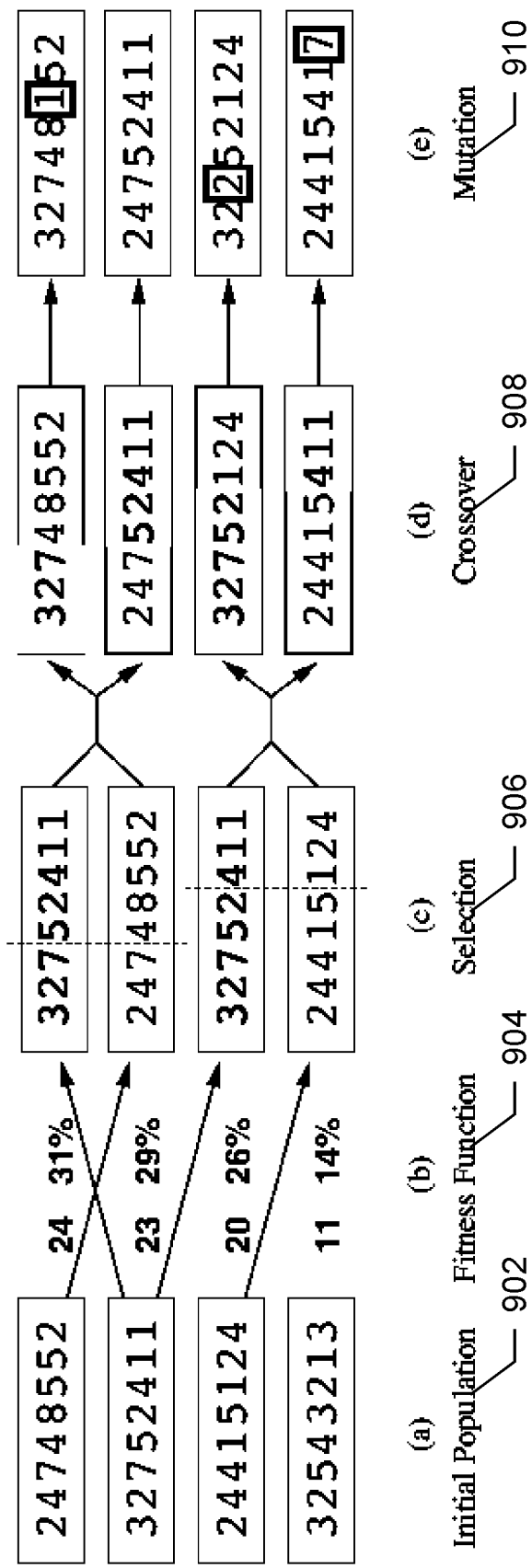
FIG. 9 is an exemplary illustration of a genetic algorithm applied to digit strings, according to embodiments of the present systems and methods.

An exemplary, simple, intuitive, one-dimensional representation of this family of algorithms is shown in FIG. 8. In this example, elevation corresponds to the objective function and the aim is to find the global maximum of the objective function. An example of a genetic algorithm applied to digit strings is shown in FIG. 9. As shown in this example, starting with an initial population 902, a fitness function 904 may be applied and a resulting population may be selected 906. Resulting populations may be comingled using crossover 908 and mutations 910 may be applied.

A high level pseudocode example reflecting this approach is given below.

```
START
Generate the initial population
Compute fitness
REPEAT
    Selection
    Crossover
    Mutation
    Compute fitness
UNTIL population has converged
STOP
```

Another example of a similar genetic algorithm 1000 is shown in FIG. 10. The approach includes an iterative process 1100, shown in FIG. 11. Process 1100 begins with 1102, in which new modeling architectures may be obtained and/or generated based on selection, crossover, and mutation. At 1104, the obtained configurations may be trained. At 1106, the surviving configurations may be selected based on how well they perform on a validation set. At 1108, the best architectures at every iteration will mutate to generate new architectures.

Figure 11:
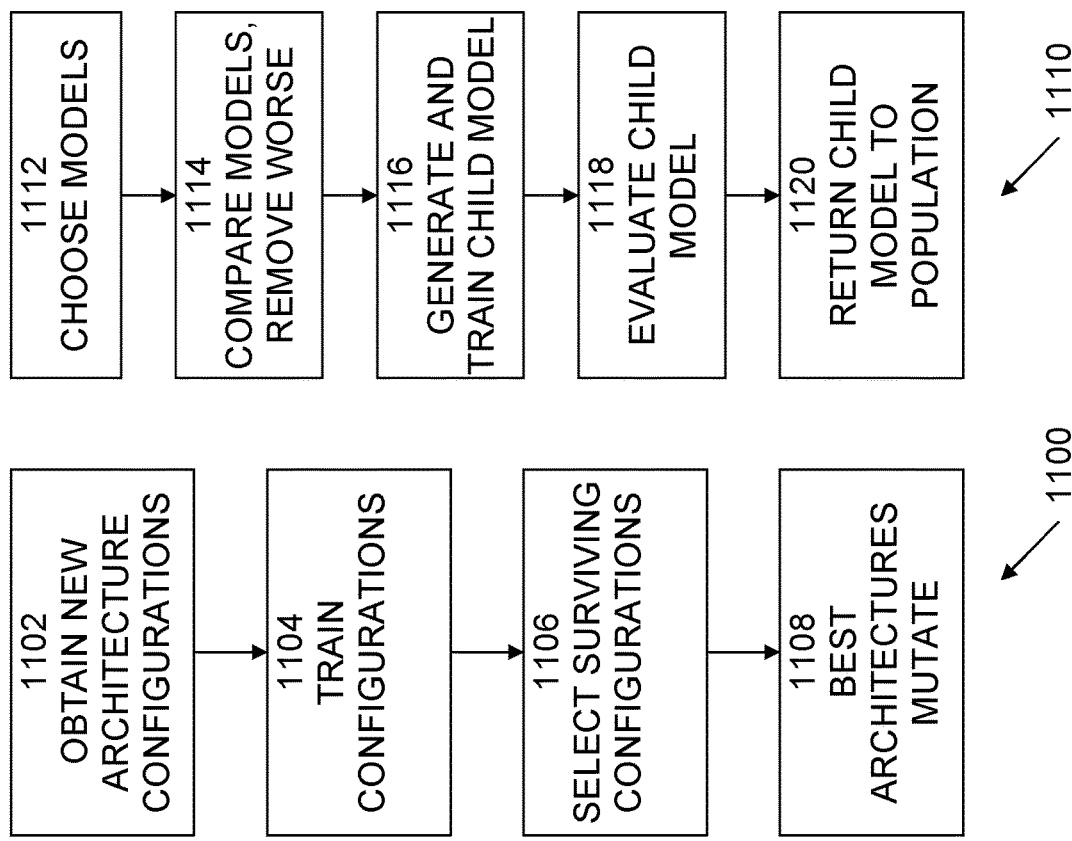
FIG. 11 shows exemplary flow diagrams of genetic algorithms, according to embodiments of the present systems and methods.

There are multiple options in terms of how the genetic algorithm may be implemented. For a deep neural net, an embodiment of a possible approach 1110 is shown in FIG. 11. The goal is to obtain an evolved population of models, each of which is a trained network architecture. At 1110 of process 1100, at each evolutionary step, two models may be chosen at random from the population. At 1112, the fitness of the two models may be compared and the worse model may be removed from population. At 1116, the better model may be chosen to be a parent for another model, through a chosen mechanism, such as mutation, and the child model may be trained. At 1118, the child model may be evaluated on a validation data set. At 1120, the child model may be put back in the population and may be free to give birth to other models in following iterations.

A large set of features may be optimized using genetic algorithms. Although originally genetic algorithms were used to evolve only the weights of a fixed architecture, since then genetic algorithms have been extended also to add connections between existing nodes, insert new nodes, recombine models, insert, or remove whole node layers, and may be used in conjunction with other approaches, such as back-propagation.

In embodiments, Support Vector Machine (SVM) models may be use. At its core, SVM represents a quadratic programming problem that uses a separated subset of the training data as support vectors for the actual training.

A support vector machine may construct a hyperplane or set of hyperplanes in a high or infinite dimensional space, which may be used for classification, regression, or other types of tasks. Intuitively, a good separation may be achieved by the hyperplane that has the largest distance to the nearest training data points of any class (so-called functional margin), since in general the larger the margin the lower the generalization error of the classifier.

SVM solves the following problem:

$$\min_{w,b,\zeta} \frac{1}{2} w^T w + C \sum_{i=1}^{n} \zeta_i$$

$$\text{subject to } y_i(w^T \phi(x_i) + b) \geq 1 - \zeta_i,$$

$$\zeta_i \geq 0, i = 1, \ldots, n$$

for binary training vectors $x_i \in \mathbb{R}^p$, and a vector $y \in \{1, -1\}^n$.

The SVM model may be effective in high dimensional spaces (which gives the possibility of representing the problem formalization in more complex manner), and with smaller data sets (this is important because the existing research corpus has its limits in terms of availability and size). Different approaches may be chosen for multi-class problem classifications ("one against one", "one vs the rest"), and different kernels may also be selected (linear, polynomial, rbf, sigmoid). In embodiments, a set of SVM models may be trained on a dataset that has as its features the problem characteristics and as its labels the solution module's characteristics. This may be done in a hierarchical way, so that different features of the solution may be predicted (model type, model morphology, model parameters, etc.).

Bayesian Networks. Embodiments may frame the problem of finding a suitable model for a problem in terms of an agent which tries to find the best action using a belief state in a given environment. Exemplary pseudocode for this formulation is presented below:

```
function DT-AGENT(percept) returns an action
    persistent: belief_state, probabilistic beliefs about the
    current state of the world
        action, the agent's action
    update belief_state based on action and percept
    calculate outcome probabilities for actions,
        given action descriptions and current belief_state
    select action with highest expected utility
        given probabilities of outcomes and utility information
    return action
```

This brings us to a new perspective, which directly highlights the uncertainty present in the task at hand, through the belief_state. Building on the known Bayesian Rule:

$$P(\text{cause} | \text{efeect}) = \frac{P(\text{effect} | \text{cause}) P(\text{cause})}{P(\text{effect})}$$

we can use probabilistic networks for creating a module that is able to handle the uncertainty in the task in a more controlled manner.

A Bayesian network is a statistical model that represents a set of variables and their conditional dependencies. In embodiments, a Bayesian network may represent the probabilistic relationships between input data, situational context and processing objective, and model types and morphologies. The network may be used to compute the probabilities of a model configuration being a good fit for a given problem formulation.

For example, given a problem formulation with two parameters A and B, we can use Bayesian networks to compute what is the probability that model M is a good candidate, given A and B. This may be formulated as shown at 1202 in FIG. 12.

For the simple independent causes network above we can write: p(M,A,B)=p(M|A,B) p(A) p(B). It can be seen in the relationship above, features A and B are independent causes, but become dependent once M is known.

Figure 12:
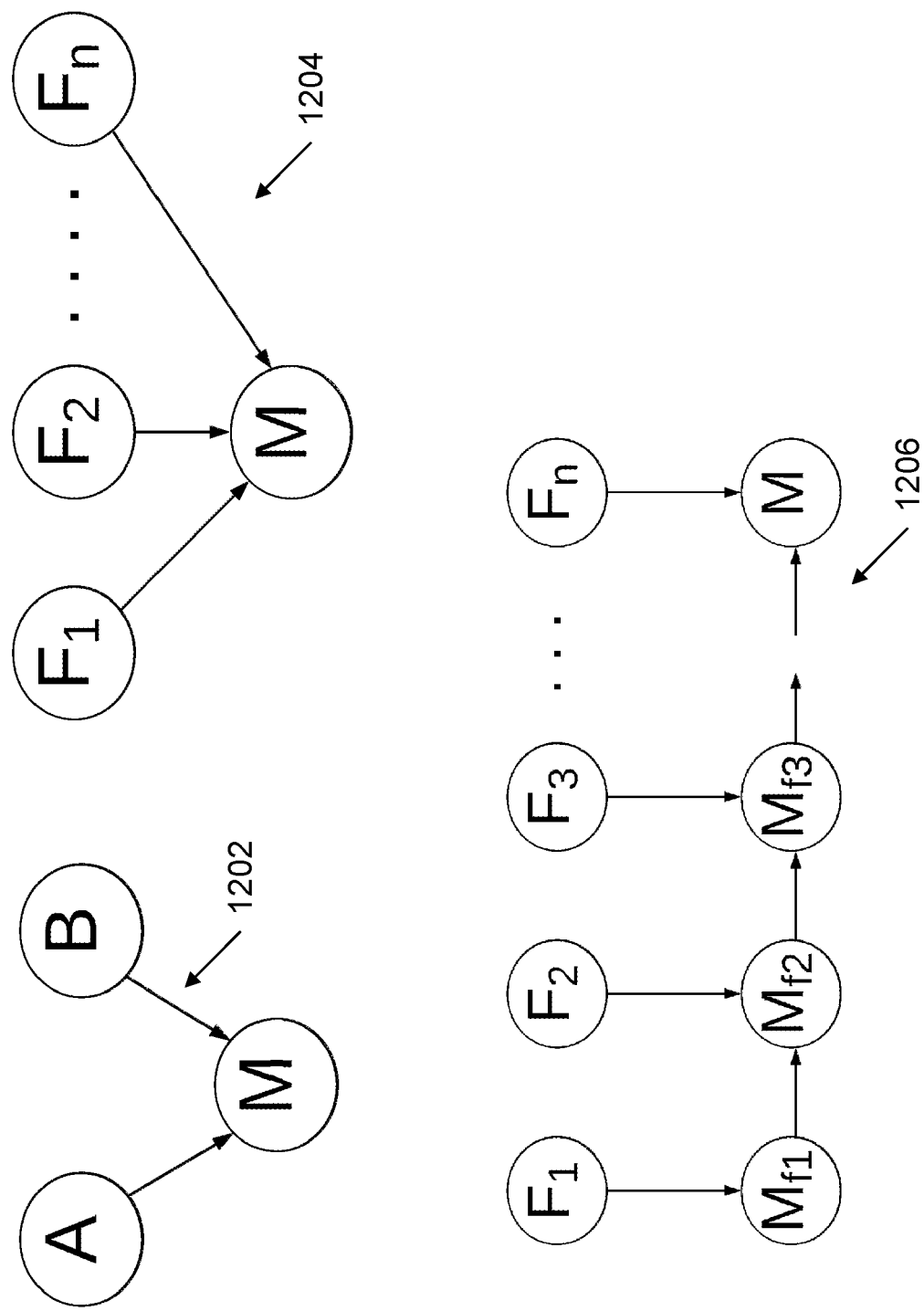
FIG. 12 is an exemplary illustration of Bayesian networks, according to embodiments of the present systems and methods.

Embodiments may utilize various configurations that can be used for creating the Bayesian belief networks to determine the most appropriate model given the problem formulation features. For example, a converging belief network connection 1204 is shown in FIG. 12. The problem can also be defined as a chain of Mf related variables representing different features of the needed model, each corresponding to a single cause representing different features of the problem formulation, as shown at 1206 in FIG. 12. Network 1206 uses parallel causal independence. In this way, the final state of the model M is dependent on its previous values.

Figure 13:
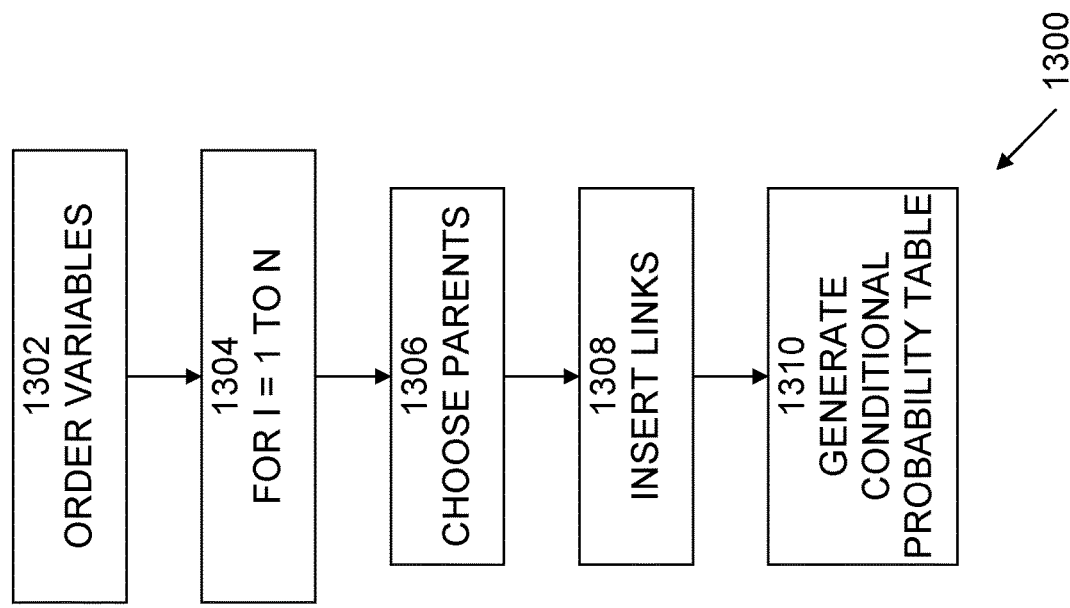
FIG. 13 is an exemplary flow diagram of a process of constructing a Bayesian network, according to embodiments of the present systems and methods.

Embodiments may construct Bayesian Networks using a process 1300, shown in FIG. 13. A mathematical representation is shown below:

$$P(x_1, \ldots, x_n) = P(x_n | x_{n-1}, \ldots, x_1) P(x_{n-1}, \ldots, x_1)$$

$$P(x_1, \ldots, x_n) = \prod_{i=1}^{n} P(x_i | \text{parents}(X_i))$$

$$P(x_1, \ldots, x_n) = P(x_n | x_{n-1}, \ldots, x_1) P(x_{n-1} | x_{n-2}, \ldots, x_1) \ldots P(x_2 | x_1) P(x_1)$$

$$= \prod_{i=1}^{n} P(x_i | x_{i-1}, \ldots, x_1).$$

$$\ldots$$

$$P(X_i | X_{i-1}, \ldots, X_1) = P(X_i | \text{Parents}(X_i))$$

Process 1300 may determine the set of variables that are required to model the domain. At 1302, the variables $\{X_1, \ldots, X_n\}$ may be ordered such that causes precede effects, for example, according to $P(x_1, \ldots, x_n) = P(x_n | x_{n-1}, \ldots, x_1)$. At 1304, for i=1 to n, 1306 to 1310 may be performed. At 1306, a minimal set of parents for $X_i$ may be chosen, such that $P(X_i | X_{i-1}, \ldots, X_1) = P(X_i | \text{Parents}(X_1))$. At 1308, for each parent, a link may be inserted from the parent to $x_i$. At 1310, a conditional probability table, $P(X_i | \text{Parents}(X_1))$ may be generated.

Figure 14:
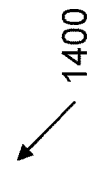
FIG. 14 is an exemplary pseudocode diagram of an Enumeration-Ask process, according to embodiments of the present systems and methods.

In order to answer queries on the network, for example, embodiments may use a version of the Enumeration-Ask process 1400, shown in FIG. 14. Likewise, for inference on the network, embodiments may use a different version 1500, shown in FIG. 15.

Exact inference complexity may depend on the type of network, accordingly, embodiments may use approximate inference to reduce complexity. For example, approximate inference processes such as Direct Sampling, Rejection Sampling, and Likelihood Weighting may be used. An example of a Likelihood Weighting process 1600 is shown in FIG. 16.

Instead of generating each sample from scratch, embodiments may use Monte Carlo Markov Chain algorithms, to generate each sample by making a random change to the preceding one. For example, Gibbs Sampling 1700, shown in FIG. 17, is such a starting point approach. A mathematical representation 1702 of Gibbs sampling is also shown.

Embodiments may estimate any desired expectation by ergodic averages—computing any statistic of a posterior distribution using N simulated samples from that distribution:

$$E[f(s)]_{\mathcal{P}} \approx \frac{1}{N} \sum_{i=1}^{N} f(s^{(i)})$$

where $\mathcal{P}$ is the posterior distribution of interest, f(s) is the desired expectation, and $f(s^{(i)})$ is the ith simulated sample from $\mathcal{P}$.

Model Combination. For any given situation, Selector 452 may not be constrained to using a single model, but may activate a combination of models for ensemble learning, for example, to minimize bias and variance. Embodiments may use various tools to determine models to combine. For example, embodiments may use cosine similarity, in which the results from different models are represented on a normalized vector space. The general formula for cosine similarity is:

$$\vec{a} \cdot \vec{b} = \|\vec{a}\| \|\vec{b}\| \cos\theta$$

$$\cos\theta = \frac{\vec{a} \cdot \vec{b}}{\|\vec{a}\| \|\vec{b}\|}$$

Accordingly, cos θ may be used as a metric of congruence between different models. However, embodiments may also use less correlated models, which learn different things, to broaden the applicability of the solution.

Intention Awareness Manifestation (IAM). Embodiments may provide an intelligent system for the definition, inference and extraction of the user's intent and aims using a comprehensive reasoning framework for determining user intents.

User intent identification becomes significantly important with the increase in technology, the expansion of digital economies and products and diversity in user preferences, which positions a user as a key actor in a system of decisions. Interpretation of such decisions or intent inference may lead to a more open, organized, and optimized society where products and services may be easily adapted and offered based on a forecast of user intent and preferences, such as provided by a recommendation system. Crime and social decay may be prevented using data and intent analysis, such as provided by a prevention system, and the common good may be pursued by optimizing every valuable aspect of user's dynamic lifestyle, such as provided by a lifestyle optimization system. Embodiments may provide these features both at the level of the community and of the individual.

Embodiments of the present systems and methods may be well suited to providing IAM functionality due to the large diversity of data channels and types together with the high complexity and interrelatedness of different ontologies that are involved.

Figure 18:
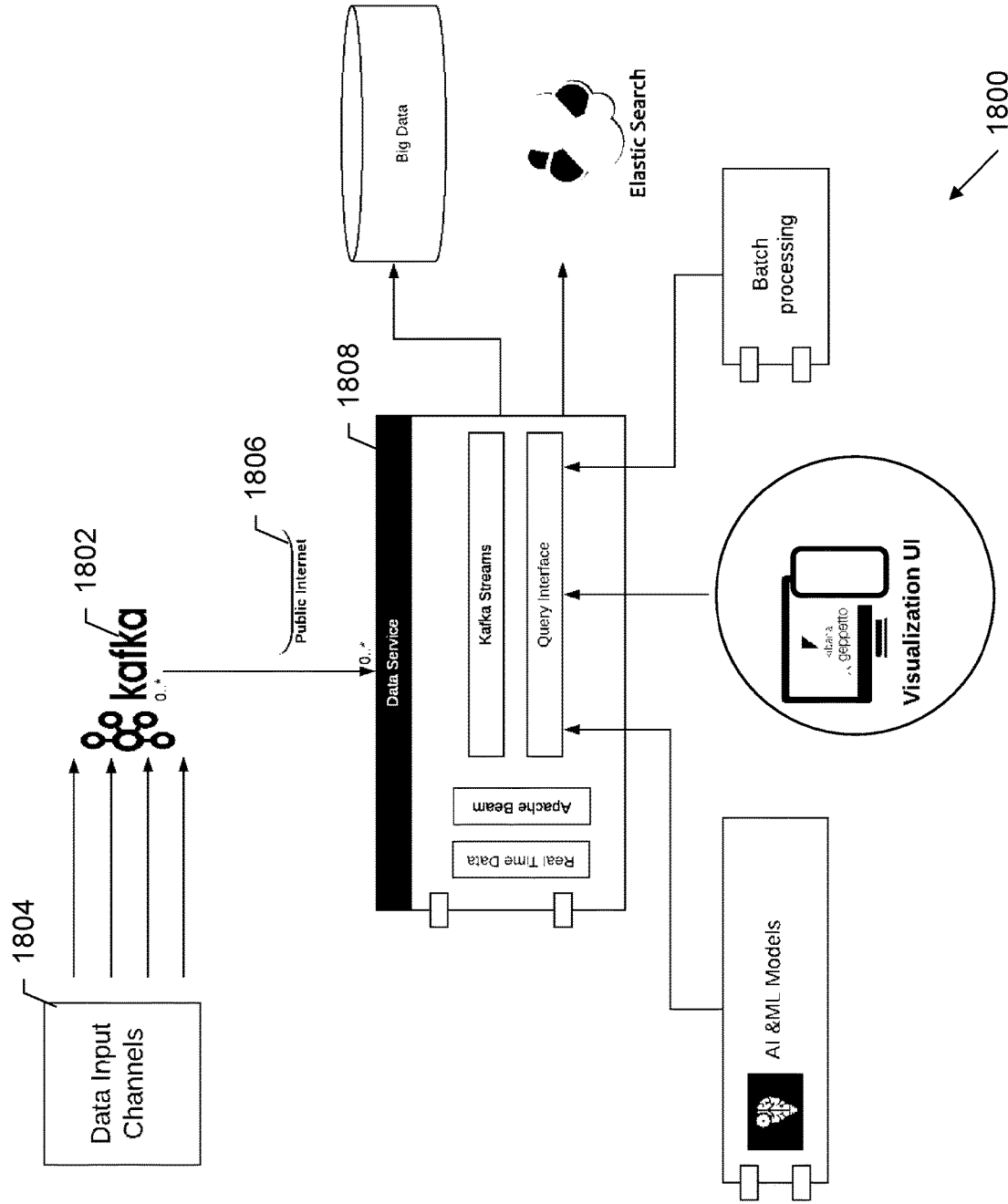
FIG. 18 is an exemplary block diagram of Data ingestion and data processing, according to embodiments of the present systems and methods.

An exemplary embodiment 1800 of architecture and the components that may provide data ingestion and data processing is shown in FIG. 18. This architecture and the components are merely examples. Embodiments may utilize other architectures and components as well.

As shown in the example of FIG. 18, embodiments may include, stream-processing software 1802, such as Apache Kafka, for data streaming and ingestion. Stream-processing software 1802 may provide real-time data pipelines and streaming apps, and may be horizontally scalable, fault-tolerant, and very fast.

Data coming from different input channels 1804 may be distributed for processing over, for example, the Internet 1806, to Data Processing Service 1808, which may be implemented in the Cloud. Embodiments may deploy Data Processing Service 1808 in one or more nodes.

Embodiments may be implemented using, for example, Apache Kafka Security with its versions TLS, Kerberos, and SASL, which may help in implementing a highly secure data transfer and consumption mechanism.

Embodiments may be implemented using, for example, Apache Kafka Streams, which may ease the integration of proxies and Data Processing Service 1808.

Embodiments may be implemented using, for example, Apache Beam, which may unify the access for both streaming data and batch processed data. It may be used by the real time data integrators to visualize and process the real time data content.

Embodiments may utilize a high volume of data and may have large data upload and retrieval performance requirements. Embodiments may use a variety of database technologies, such as OpenTSDB ("OpenTSDB—A Distributed, Scalable Monitoring System"), Timescale ("OpenTSDB—A Distributed, Scalable Monitoring System", "Timescale|an Open-Source Time-Series SQL Database Optimized for Fast Ingest, Complex Queries and Scale"), BigQuery ("BigQuery—Analytics Data Warehouse|Google Cloud"), HBase ("Apache HBase—Apache HBase™ Home"), HDF5 ("HDF5®—The HDF Group"), etc.

Embodiments may be implemented using, for example, Elasticsearch, which may be used as a second index to retrieve data based on different filtering options. Embodiments may be implemented using, for example, Geppetto UI widgets, which may be used for visualizing resources as neuronal activities. Embodiments may be implemented using, for example, Kibana, which is a charting library that may be used on top of Elasticsearch for drawing all types of graphics: bar charts, pie charts, time series charts etc.

Implementation Languages. Embodiments may be implemented using a variety of computer languages. For example, components may be implemented using Scala, Haskell, and/or Clojure, Julia, C++, Domain Specific Languages, Python, etc.

Implementation Details. Embodiments may be deployed, for example, on three layers of computing infrastructure: 1) a sensors layer equipped with minimal computing capability may be utilized to accommodate simple tasks (such as average, minimum, maximum), 2) a gateway layer equipped with medium processing capability and memory may be utilized to deploy a pre-trained neural network (approximated values), and 3) a cloud layer possessing substantial processing capability and storage may be utilized to train the models and execute complex tasks (simulations, virtual reality etc.).

Embodiments may employ a diverse range of approximation methods, such as Parameter Value Skipping, Loop Reduction and Memory Access Skipping or others greatly facilitation reduction in complexity and adaptation for non-cloud deployment, such as the gateway layer. The entire processing plan may also utilize techniques from Software Defined Network Processing, Edge Computing Techniques, such as Network Data Analysis and History Based Processing Behaviors Learning using Smart Routers.

In embodiments, the three layer computing infrastructure (cloud, gateway, sensors) may provide flexibility and adaptability for the entire workflow. To provide the required coordination and storage, cloud computing may be used. Cloud Computing is a solution which has been validated by a community of practice as a reliable technology for dealing with complexity in workflow.

In addition to the cloud layer, embodiments may utilize Fog/Edge Computing techniques for the gateway layer and sensors layer to perform physical input (sensors) and output (displays, actuators, and controllers). Embodiments may create small cloud applications, Cloudlets, closer to the data capture points, or nearer to the data source and may be compared with centralized Clouds for determining benefits in terms of costs and quality-of-results. By nature, these cloudlets may be nearer to the data sources and thus minimize network cost.

This method will also enable the resources to be used more judiciously, as idling computing power (CPUs, GPUs, etc.) and storage can be recruited and monetized. These methods have been validated in Volunteer Computing which has been used primarily in academic institutions and in community of volunteers (such as BOINC).

For example, in embodiments, Solution Processor component 456, which runs the solution modules, may be mapped to 3 different layers: (i) sensors layer (edge computing), (ii) gateway layers (in-network processing) and (iii) cloud layer (cloud processing). Starting with sensors layer, the following two layers (gateway layers and cloud layers) may add more processing power but also delay to the entire workflow, therefore depending on task objectives, different steps of the solution plan can be mapped to run on different layers.

Edge Computing implies banks of low power I/O sensors and minimal computing power; In-Network Processing can be pursued via different gateway devices (Phones, Laptops, GPU Routers) which offer medium processing and memory capabilities; Cloud Computing may provide substantial computation and storage.

In embodiments, the learning modules may be optimized for the available computing resources. If computing clusters are used, models may be optimized for speed, otherwise, a compromise between achieving a higher accuracy and computing time may be made.

Figure 19:
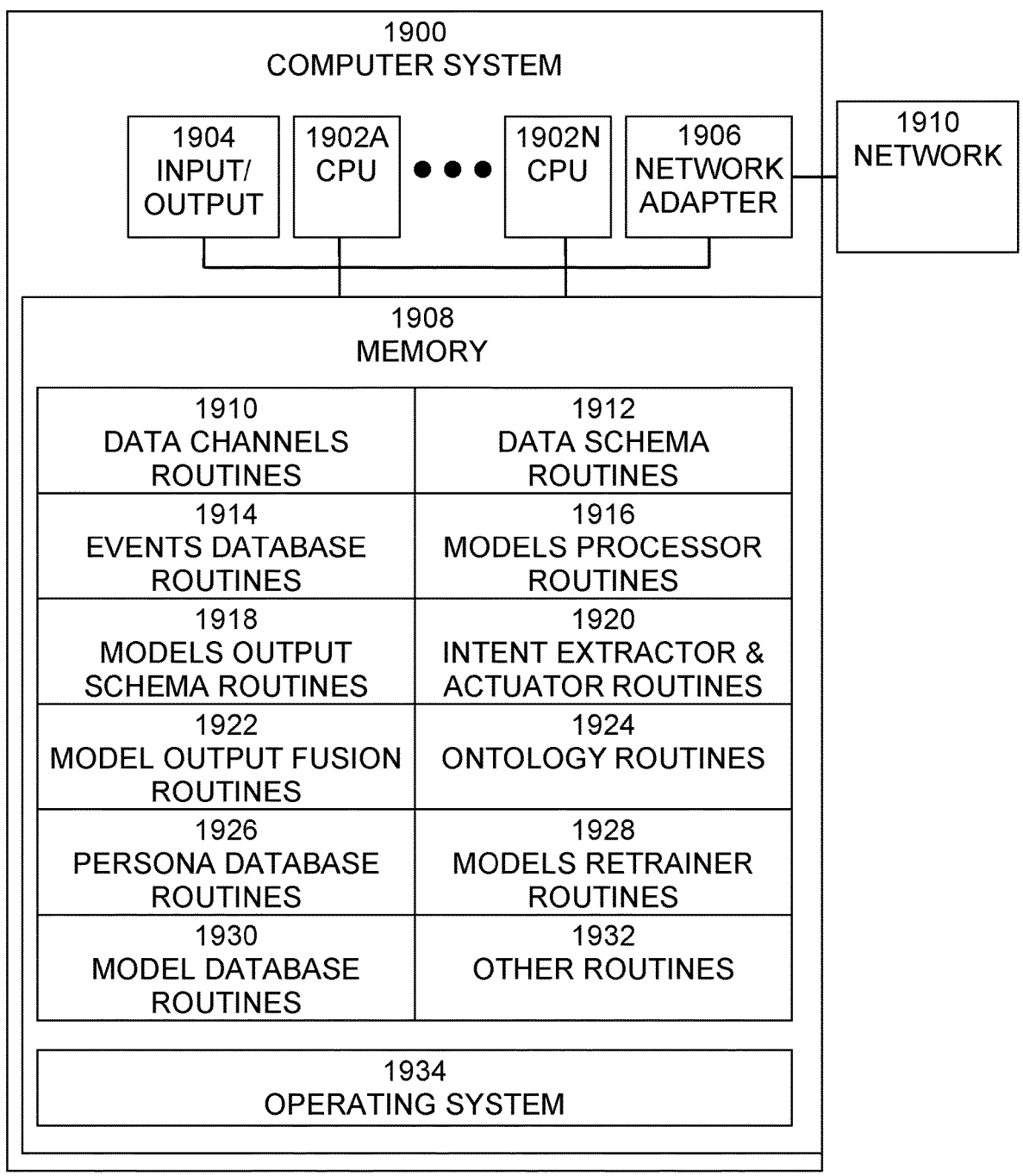
FIG. 19 is an exemplary block diagram of a computer system, in which processes involved in the embodiments described herein may be implemented.

An exemplary block diagram of a computer system 1900, in which processes involved in the embodiments described herein may be implemented, is shown in FIG. 19. Computer system 1900 may be implemented using one or more programmed general-purpose computer systems, such as embedded processors, systems on a chip, personal computers, workstations, server systems, and minicomputers or mainframe computers, or in distributed, networked computing environments. Computer system 1900 may include one or more processors (CPUs) 1902A-1902N, input/output circuitry 1904, network adapter 1906, and memory 1908. CPUs 1902A-1902N execute program instructions in order to carry out the functions of the present communications systems and methods. Typically, CPUs 1902A-1902N are one or more microprocessors, such as an INTEL CORE® processor. FIG. 19 illustrates an embodiment in which computer system 1900 is implemented as a single multi-processor computer system, in which multiple processors 1902A-1902N share system resources, such as memory 1908, input/output circuitry 1904, and network adapter 1906. However, the present communications systems and methods also include embodiments in which computer system 1900 is implemented as a plurality of networked computer systems, which may be single-processor computer systems, multi-processor computer systems, or a mix thereof.

Input/output circuitry 1904 provides the capability to input data to, or output data from, computer system 1900. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 1906 interfaces device 1900 with a network 1910. Network 1910 may be any public or proprietary LAN or WAN, including, but not limited to the Internet.

Memory 1908 stores program instructions that are executed by, and data that are used and processed by, CPU 1902 to perform the functions of computer system 1900. Memory 1908 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 1908 may vary depending upon the function that computer system 1900 is programmed to perform. In the example shown in FIG. 19, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In the example shown in FIG. 19, memory 1908 may include data channels routines 1910, data schema routines 1912, events database routines 1914, models processor routines 1916, models output schema routines 1918, intent extractor & actuator routines 1920, model output fusion routines 1922, ontology routines 1924, persona database routines 1926, models retrainer routines 1928, model database routines 1930, other routines 1932, and operating system 1934. Data channels routines 1910 may include software to perform the functions of data channels block 401, as described above. Data schema routines 1912 may include software to perform the functions of data schema block 402, as described above. Events database routines 1914 may include software to perform the functions of events database block 403, as described above. Models processor routines 1916 may include software to perform the functions of models processor block 404, as described above. Models output schema routines 1918 may include software to perform the functions of models output schema block 424, as described above. Intent extractor & actuator routines 1920 may include software to perform the functions of intent extractor & actuator block 425, as described above.

Model output fusion routines 1922 may include software to perform the functions of model output fusion block 426, as described above. Ontology routines 1924 may include software to perform the functions of ontology block 436, as described above. Persona database routines 1926 may include software to perform the functions of persona database block 437, as described above. Models retrainer routines 1928 may include software to perform the functions of models retrainer block 438, as described above. Model database routines 1930 may include software to perform the functions of model database block 448, as described above. Other routines 1932 may include software to perform the other functions of embodiments of the present systems and methods, as described above. Other operating system routines 1934 may provide additional system functionality.

As shown in FIG. 19, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method implemented in a computer comprising a processor, memory accessible by the processor, and computer program instructions stored in the memory and executable by the processor, the method comprising:
   receiving, at the computer system, data capturing an event;
   generating, at the computer system, a narrativization of the data characterizing the event captured in the data, wherein generating the narrativization comprises captioning, at the computer system, image data, captioning, at the computer system, video data, recognizing, at the computer system, speech included in audio data, generating summary data, at the computer system, characterizing text data, and generating summary data, at the computer system, characterizing sensor data;
   detecting, at the computer system, at least one entity involved in the event captured in the data, wherein the at least one entity comprises at least one of an object, activity, situation, and person detected from the image data, video data, speech included in audio data, text data, and sensor data;

obtaining, at the computer system, ontology information based on the generated narrativization and the detected at least one entity, wherein the ontology information includes concepts and categories relating to users and data showing properties and relations between the users and user's data, real world data, concepts and categories relating to a context of data including data showing properties and relations between the contexts and the other data, concepts and categories relating to intents of monitored entities including data showing properties and the relations between the monitored entities, actions of the monitored entities, and characteristics of the monitored entities;

determining, at the computer system, an intent of the at least one detected entity involved in the event captured in the data, wherein the intent is determined using the generated captioning of the image data, the generated captioning of the video data, the recognized speech included in the audio data, the generating summary data characterizing the text data, and the generated summary data characterizing the sensor data, the at least one entity detected from the image data, video data, speech included in audio data, text data, and sensor data, and the ontology information obtained based on the generated narrativization and the detected at least one entity;

classifying the determined intent based on duration according to Strategic Intent: that which the user wants to achieve over the long-term in a specific domain, and Tactical Intent: that which the user wants to achieve over the short-term, and based on form of expression according to Explicit Intent: the intent is explicitly presented to the system and can be directly detected, and Implicit Intent: the intent is to be derived from one or a combination of data sources that do not express the intent directly; and performing, at the computer system, an action responsive to the determined intent, wherein the action responsive to the determined intent is determined using an intent extractor and actuator to infer an appropriate action for a given situation and an overall goal of a use case.

2. The method of claim 1, wherein the data capturing an event comprises at least one of image data, video data, text data, audio data, and sensor data.

3. The method of claim 2, wherein the data capturing an event comprises at least one of real-time data relating to events occurring contemporaneously and stored data relating events that occurred in the past.

4. The method of claim 1, wherein detecting at least one entity comprises:

detecting, at the computer system, the at least one entity comprising at least one of an object, activity, situation, and person from image data using at least one of image object recognition models, image movement recognition models, image facial recognition models, and image situation recognition models;

detecting, at the computer system, the at least one entity comprising at least one of an object, activity, situation, and person from video data using at least one of video object recognition models, video movement recognition models, video facial recognition models, and video situation recognition models;

detecting, at the computer system, the at least one entity comprising at least one of an object, activity, situation, and person from audio data using at least one of audio object recognition models, audio movement recognition models, audio speaker recognition models, and audio situation recognition models;

detecting, at the computer system, the at least one entity comprising at least one of an object, activity, situation, and person from text data using at least one of text object recognition models, text activity recognition models, text situation recognition models, and text person recognition models; and detecting, at the computer system, the at least one entity comprising at least one of an object, activity, situation, and person from text data using at least one of sensor object recognition models, sensor activity recognition models, sensor situation recognition models, and sensor person recognition models.

5. A computer system comprising a processor, memory accessible by the processor, and computer program instructions stored in the memory and executable by the processor to perform:

receiving data capturing an event;

generating a narrativization of the data characterizing the event captured in the data, wherein generating the narrativization comprises captioning, at the computer system, image data, captioning, at the computer system, video data, recognizing, at the computer system, speech included in audio data, generating summary data, at the computer system, characterizing text data, and generating summary data, at the computer system, characterizing sensor data;

detecting at least one entity involved in the event captured in the data, wherein the at least one entity comprises at least one of an object, activity, situation, and person detected from the image data, video data, speech included in audio data, text data, and sensor data;

obtaining ontology information based on the generated narrativization and the detected at least one entity, wherein the ontology information includes concepts and categories relating to users and data showing properties and relations between the users and user's data, real world data, concepts and categories relating to a context of data including data showing properties and relations between the contexts and the other data, concepts and categories relating to intents of monitored entities including data showing properties and the relations between the monitored entities, actions of the monitored entities, and characteristics of the monitored entities;

determining an intent of the at least one detected entity involved in the event captured in the data, wherein the intent is determined using the generated captioning of the image data, the generated captioning of the video data, the recognized speech included in the audio data, the generating summary data characterizing the text data, and the generated summary data characterizing the sensor data, the at least one entity detected from the image data, video data, speech included in audio data, text data, and sensor data, and the ontology information obtained based on the generated narrativization and the detected at least one entity;

classifying the determined intent based on duration according to Strategic Intent: that which the user wants to achieve over the long-term in a specific domain, and Tactical Intent: that which the user wants to achieve over the short-term, and based on form of expression according to Explicit Intent: the intent is explicitly presented to the system and can be directly detected, and Implicit Intent: the intent is to be derived from one or a combination of data sources that do not express the intent directly; and performing an action responsive to the determined intent, wherein the action responsive to the determined intent is determined using an intent extractor and actuator to infer an appropriate action for a given situation and an overall goal of a use case.

6. The system of claim 5, wherein the data capturing an event comprises at least one of image data, video data, text data, audio data, and sensor data.

7. The system of claim 6, wherein the data capturing an event comprises at least one of real-time data relating to events occurring contemporaneously and stored data relating events that occurred in the past.

8. The system of claim 5, wherein detecting at least one entity comprises:
  detecting the at least one entity comprising at least one of an object, activity, situation, and person from image data using at least one of image object recognition models, image movement recognition models, image facial recognition models, and image situation recognition models;
  detecting the at least one entity comprising at least one of an object, activity, situation, and person from video data using at least one of video object recognition models, video movement recognition models, video facial recognition models, and video situation recognition models;
  detecting the at least one entity comprising at least one of an object, activity, situation, and person from audio data using at least one of audio object recognition models, audio movement recognition models, audio speaker recognition models, and audio situation recognition models;
  detecting the at least one entity comprising at least one of an object, activity, situation, and person from text data using at least one of text object recognition models, text activity recognition models, text situation recognition models, and text person recognition models; and
  detecting the at least one entity comprising at least one of an object, activity, situation, and person from text data using at least one of sensor object recognition models, sensor activity recognition models, sensor situation recognition models, and sensor person recognition models.

9. A computer program product comprising a non-transitory computer readable storage having program instructions embodied therewith, the program instructions executable by a computer, to cause the computer to perform a method comprising:
  receiving, at the computer system, data capturing an event;
  generating, at the computer system, a narrativization of the data characterizing the event captured in the data, wherein generating the narrativization comprises captioning, at the computer system, image data, captioning, at the computer system, video data, recognizing, at the computer system, speech included in audio data, generating summary data, at the computer system, characterizing text data, and generating summary data, at the computer system, characterizing sensor data;
  detecting, at the computer system, at least one entity involved in the event captured in the data, wherein the at least one entity comprises at least one of an object, activity, situation, and person detected from the image data, video data, speech included in audio data, text data, and sensor data;
  obtaining, at the computer system, ontology information based on the generated narrativization and the detected at least one entity, wherein the ontology information includes concepts and categories relating to users and data showing properties and relations between the users and user's data, real world data, concepts and categories relating to a context of data including data showing properties and relations between the contexts and the other data, concepts and categories relating to intents of monitored entities including data showing properties and the relations between the monitored entities, actions of the monitored entities, and characteristics of the monitored entities;
  determining, at the computer system, an intent of the at least one detected entity involved in the event captured in the data, wherein the intent is determined using the generated captioning of the image data, the generated captioning of the video data, the recognized speech included in the audio data, the generating summary data characterizing the text data, and the generated summary data characterizing the sensor data, the at least one entity detected from the image data, video data, speech included in audio data, text data, and sensor data, and the ontology information obtained based on the generated narrativization and the detected at least one entity;
  classifying the determined intent based on duration according to Strategic Intent: that which the user wants to achieve over the long-term in a specific domain, and Tactical Intent: that which the user wants to achieve over the short-term, and based on form of expression according to Explicit Intent: the intent is explicitly presented to the system and can be directly detected, and Implicit Intent: the intent is to be derived from one or a combination of data sources that do not express the intent directly; and
  performing, at the computer system, an action responsive to the determined intent, wherein the action responsive to the determined intent is determined using an intent extractor and actuator to infer an appropriate action for a given situation and an overall goal of a use case.

10. The computer program product of claim 9, wherein the data capturing an event comprises at least one of image data, video data, text data, audio data, and sensor data.

11. The computer program product of claim 10, wherein the data capturing an event comprises at least one of real-time data relating to events occurring contemporaneously and stored data relating events that occurred in the past.

12. The computer program product of claim 9, wherein detecting at least one entity comprises:
  detecting, at the computer system, the at least one entity comprising at least one of an object, activity, situation, and person from image data using at least one of image object recognition models, image movement recognition models, image facial recognition models, and image situation recognition models;
  detecting, at the computer system, the at least one entity comprising at least one of an object, activity, situation, and person from video data using at least one of video object recognition models, video movement recognition models, video facial recognition models, and video situation recognition models;

detecting, at the computer system, the at least one entity comprising at least one of an object, activity, situation, and person from audio data using at least one of audio object recognition models, audio movement recognition models, audio speaker recognition models, and audio situation recognition models;

detecting, at the computer system, the at least one entity comprising at least one of an object, activity, situation, and person from text data using at least one of text object recognition models, text activity recognition models, text situation recognition models, and text person recognition models; and detecting, at the computer system, the at least one entity comprising at least one of an object, activity, situation, and person from text data using at least one of sensor object recognition models, sensor activity recognition models, sensor situation recognition models, and sensor person recognition models.

* * * * *